(12) United States Patent
Mann et al.

(10) Patent No.: US 8,197,454 B2
(45) Date of Patent: Jun. 12, 2012

(54) FLUID CARTRIDGES AND PARTIALLY IMPLANTABLE MEDICAL DEVICES FOR USE WITH SAME

(75) Inventors: Alfred E. Mann, Las Vegas, NV (US); Tom Xiaohai He, Simi Valley, CA (US)

(73) Assignee: IncuMed, LLC, Valencia, CA (US)

( * ) Notice: Subject to any disclaimer, the term of this patent is extended or adjusted under 35 U.S.C. 154(b) by 259 days.

(21) Appl. No.: 12/390,432

(22) Filed: Feb. 21, 2009

(65) Prior Publication Data

US 2010/0217241 A1    Aug. 26, 2010

(51) Int. Cl.
*A61M 31/00* (2006.01)
(52) U.S. Cl. .................. 604/288.04; 604/67; 604/891.1
(58) Field of Classification Search ............ 604/65, 604/67, 274, 288.01–288.04, 890.1, 891.1, 604/39–45, 132, 175, 116, 117, 189
See application file for complete search history.

(56) References Cited

U.S. PATENT DOCUMENTS

| | | | |
|---|---|---|---|
| 3,739,779 A * | 6/1973 | Pfleger | 604/205 |
| 4,013,074 A | 3/1977 | Sipos | |
| 4,496,349 A | 1/1985 | Cosentino | |
| 4,581,020 A | 4/1986 | Mittleman | |
| 4,634,427 A | 1/1987 | Hannula | |
| 4,804,369 A * | 2/1989 | Lapeyre et al. | 604/175 |
| 5,147,321 A | 9/1992 | Slonina | |
| 5,256,937 A | 10/1993 | Bubeck | |
| 5,385,561 A * | 1/1995 | Cerny | 604/264 |
| 5,387,192 A | 2/1995 | Glantz | |
| 5,512,048 A | 4/1996 | Slettenmark | |
| 5,628,309 A | 5/1997 | Brown | |
| 5,891,097 A * | 4/1999 | Saito et al. | 604/141 |
| 5,954,700 A * | 9/1999 | Kovelman | 604/232 |
| 6,071,497 A | 6/2000 | Steiner | |
| 6,227,818 B1 | 5/2001 | Falk et al. | |
| 6,264,439 B1 | 7/2001 | Falk et al. | |
| 6,428,771 B1 | 8/2002 | Steiner et al. | |
| 6,659,982 B2 * | 12/2003 | Douglas et al. | 604/173 |
| 6,962,580 B2 * | 11/2005 | Adams et al. | 604/891.1 |
| 7,201,746 B2 | 4/2007 | Olsen | |
| 7,351,239 B2 | 4/2008 | Gill | |
| 7,604,617 B2 | 10/2009 | Porter et al. | |
| 7,614,545 B2 * | 11/2009 | Christoffersen et al. | 235/375 |
| 2001/0034506 A1 | 10/2001 | Hirschman | |
| 2004/0204686 A1 | 10/2004 | Porter et al. | |
| 2004/0267238 A1 | 12/2004 | Haarla | |

(Continued)

FOREIGN PATENT DOCUMENTS

WO    WO-2008/139459    11/2008

OTHER PUBLICATIONS

"Sensible". Random House Dictionary. Dictionary.com <http://dictionary.reference.com/browse/sensible.*

(Continued)

*Primary Examiner* — Kevin C Sirmons
*Assistant Examiner* — Kami A Bosworth
(74) *Attorney, Agent, or Firm* — Henricks, Slavin & Holmes LLP

(57) ABSTRACT

A fluid cartridge including a housing, a needle extending from the housing and a plurality of circumferentially spaced sensible members carried by the housing such that each of the sensible members is circumferentially spaced from the other sensible members, and apparatus including such a cartridge in combination with a partially implantable medical device.

31 Claims, 23 Drawing Sheets

U.S. PATENT DOCUMENTS

| | | | |
|---|---|---|---|
| 2005/0274377 A1 | 12/2005 | Gonda | |
| 2006/0264897 A1 | 11/2006 | Lobl | |
| 2007/0021712 A1* | 1/2007 | Bernard et al. | 604/21 |
| 2007/0112334 A1 | 5/2007 | Porter et al. | |
| 2007/0149949 A1 | 6/2007 | Porter et al. | |
| 2007/0255237 A1 | 11/2007 | Lobl | |
| 2007/0255260 A1* | 11/2007 | Haase | 604/891.1 |
| 2007/0269322 A1 | 11/2007 | Falk et al. | |
| 2008/0127970 A1 | 6/2008 | Steiner et al. | |
| 2008/0208174 A1 | 8/2008 | Johnson | |
| 2008/0306444 A1 | 12/2008 | Brister | |
| 2008/0306466 A1 | 12/2008 | Shelton | |
| 2010/0137802 A1 | 6/2010 | Yodfat | |
| 2010/0217239 A1 | 8/2010 | Mann | |
| 2010/0217240 A1 | 8/2010 | Mann | |
| 2010/0217242 A1 | 8/2010 | Mann | |
| 2010/0217243 A1 | 8/2010 | Mann | |
| 2010/0217244 A1 | 8/2010 | Mann | |
| 2011/0009807 A1* | 1/2011 | Kjeken et al. | 604/21 |

OTHER PUBLICATIONS

Sheryl Merkin et al., "The Fight Against Diabetes," TheDoctorWillSeeYouKnow.Com (Feb. 2007).

U.S. Appl. No. 12/390,425, filed Feb. 21, 2009, entitled "Partially Implantable Medical Devices and Methods."

U.S. Appl. No. 12/390,430, filed Feb. 21, 2009, entitled "Partially Implantable Medical Devices With Cartridge Movement Sensor and Associated Methods."

U.S. Appl. No. 12/390,434, filed Feb. 21, 2009, entitled "Partially Implantable Medical Devices and Delivery/Manifold Tube for Use With Same."

U.S. Appl. No. 12/390,437, filed Feb. 21, 2009, entitled "Partially Implantable Medical Devices and Treatment Methods Associated With Same."

U.S. Appl. No. 12/390,438, filed Feb. 21, 2009, entitled "Fluid Cartridges Including a Power Source and Partially Implantable Medical Devices for Use With Same."

Office Action dated Sep. 13, 2010 in U.S. Appl. No. 12/390,425.
Office Action dated Dec. 22, 2010 in U.S. Appl. No. 12/390,430.
Office Action dated Dec. 18, 2009 in U.S. Appl. No. 12/390,437.
Office Action dated Dec. 23, 2010 in U.S. Appl. No. 12/390,438.
Office Action dated Mar. 8, 2011 in U.S. Appl. No. 12/390,425.
PCT Int. Search Report and Written Opinion Dated Jun. 15, 2010 is related PCT App. No. PCT/US2010/024628.
Office Action dated May 13, 2011 in U.S. Appl. No. 12/390,430.
Office Action dated Aug. 2, 2011 in U.S. Appl. No. 12/390,438.
Office Action dated Aug. 11, 2011 in U.S. Appl. No. 12/390,434.
Office Action dated Aug. 22, 2011 in U.S. Appl. No. 12/390,430.
Office Action dated Dec. 1, 2011 in U.S. Appl. No. 12/390,434.
Office Action dated Feb. 15, 2012 in U.S. Appl. No. 12/390,430.
Notice of Allowance dated Apr. 23, 2012 in U.S. Appl. No. 12/390,430, and copy of allowed claims.

* cited by examiner

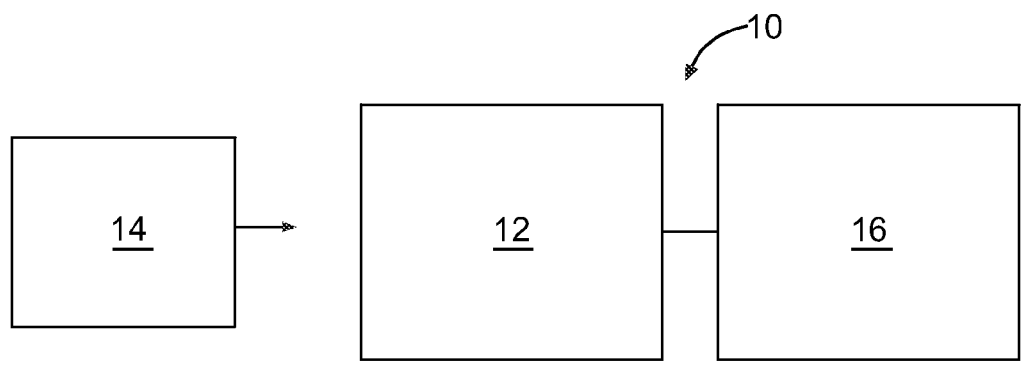
FIG. 1
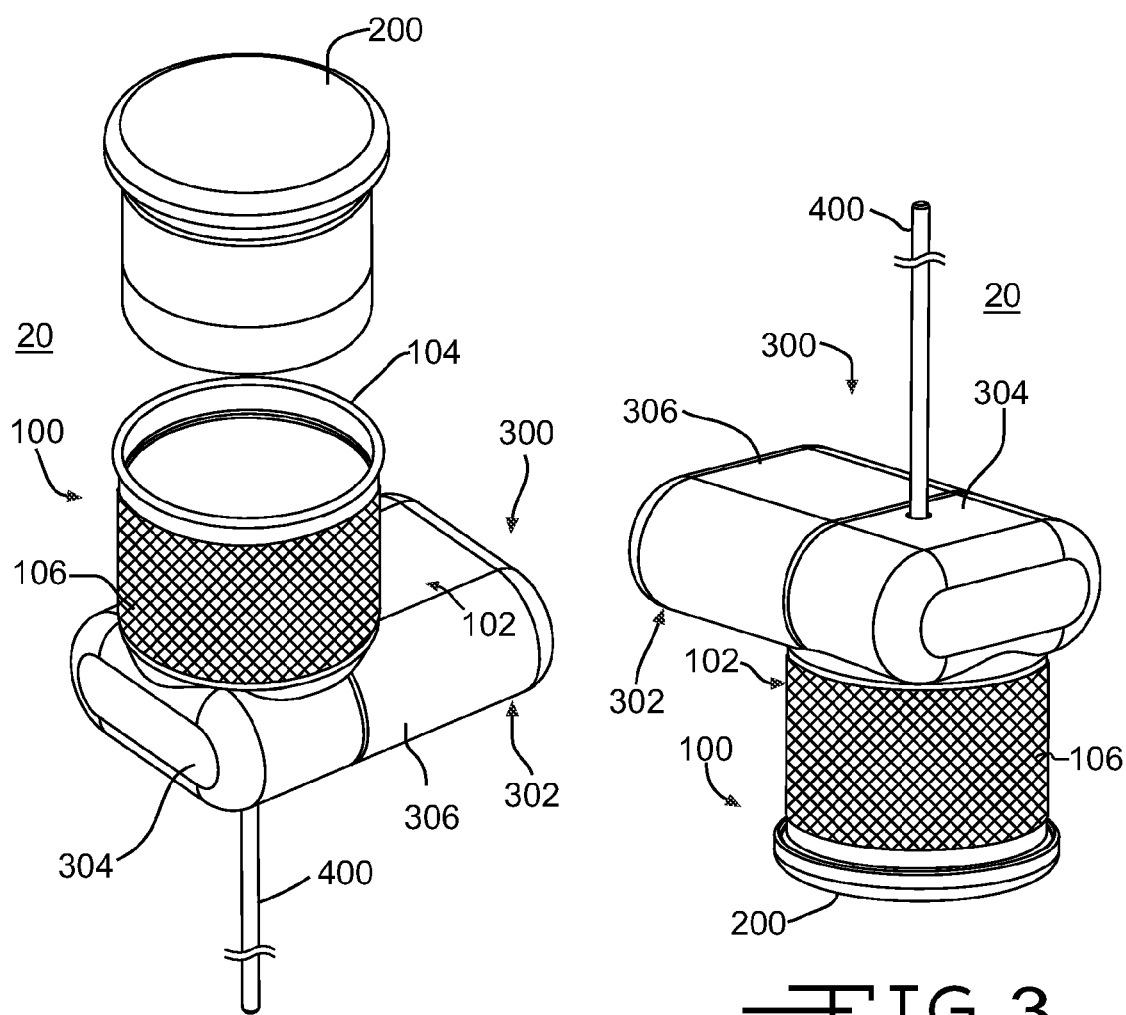
FIG. 2
FIG. 3

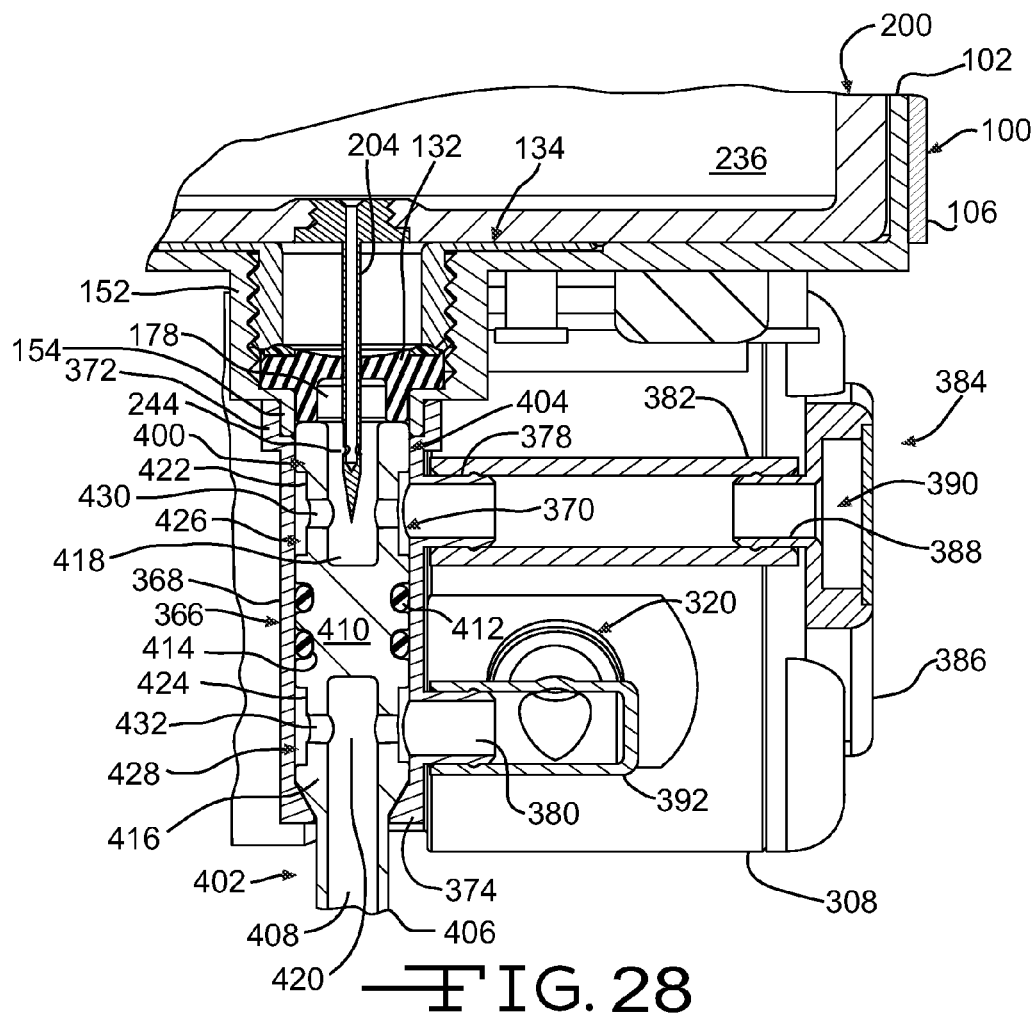

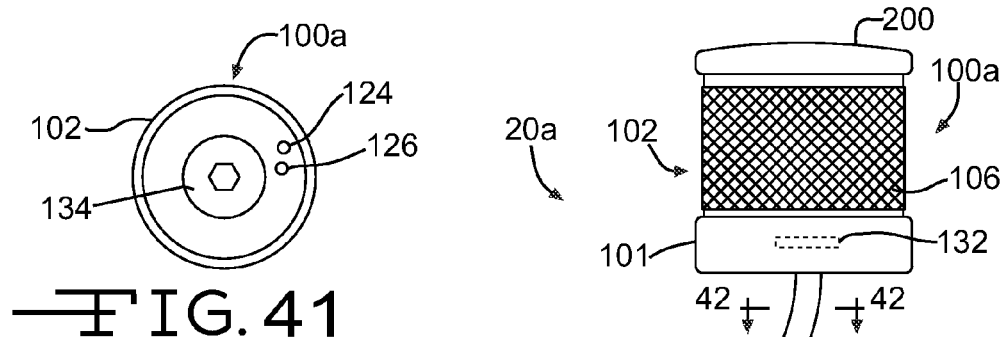
FIG. 41
FIG. 39
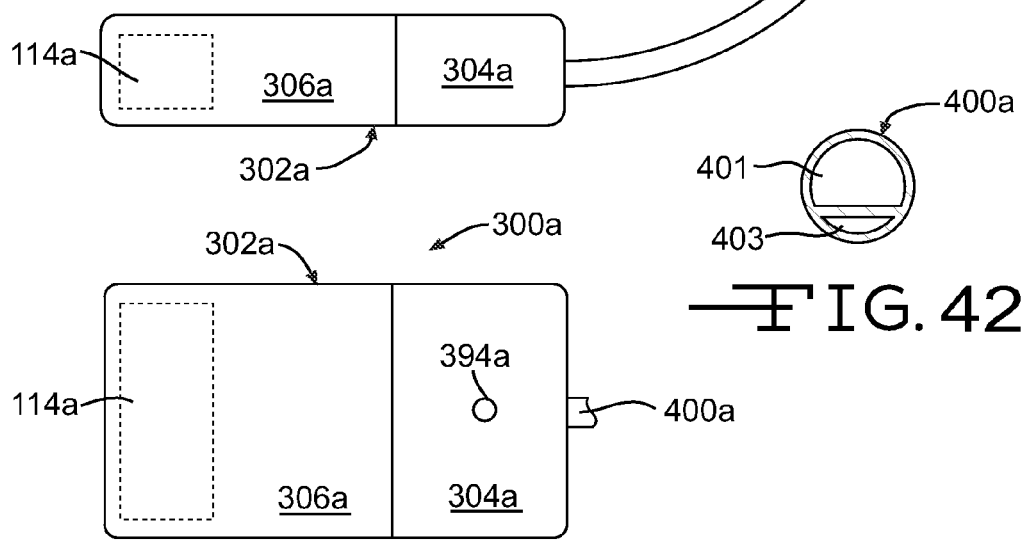
FIG. 42
FIG. 40
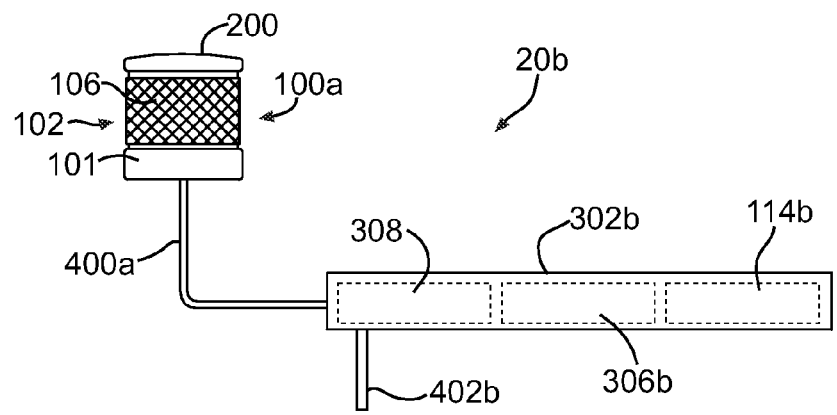
FIG. 43 ents of a present invention.
FLUID CARTRIDGES AND PARTIALLY IMPLANTABLE MEDICAL DEVICES FOR USE WITH SAME

BACKGROUND

1. Field

The present inventions relate generally to implantable medical devices.

2. Description of the Related Art

Fully implantable infusion devices, which are carried entirely within the patient's body and include a reservoir, a fluid transfer device and a battery, have been used to provide patients with a medication or other substance (collectively "infusible substance"). The reservoir is used to store the infusible substance and, in some instances, fully implantable infusion devices are provided with a fill port that allows the reservoir to be transcutaneously filled (and/or re-filled) through a hypodermic needle. The reservoir is coupled to the fluid transfer device, which is in turn connected to an outlet port. A catheter, which has an outlet at the target body region, may be connected to the outlet port. As such, infusible substance from the reservoir may be transferred from the reservoir to the target body region by way of the fluid transfer device and catheter.

The present inventors have determined that, while generally useful, there are a number of issues associated with conventional fully implantable infusion devices. For example, the present inventors have determined that conventional fully implantable infusion devices are relatively large. In particular, the batteries tend to be relatively large because they must last many years and the reservoirs tend to be relatively large in order to minimize refills, which may necessitate a visit to a physician for a percutaneous needle-based refilling procedure. Another issue identified by the present inventors relates to control. Conventional fully implantable infusion devices are controlled by way of an external remote control which can be lost or misplaced. Another issue identified by the present inventors is maintenance. Should, for example, the catheter be damaged or blocked, surgery is required to remove and replace the catheter.

SUMMARY

An apparatus in accordance with one of the present inventions includes a percutaneous port and an implantable operative portion.

An apparatus in accordance with one of the present inventions includes a housing member defining an opening, a fluid transfer device and a housing cover carried by the fluid transfer device and secured to the opening.

An apparatus in accordance with one of the present inventions includes a percutaneous port configured to receive a cartridge and an implantable operative portion, and is configured to sense movement of the cartridge relative to the percutaneous port.

A method in accordance with one of the present inventions includes the step of sensing movement of a cartridge relative to a percutaneous port.

A cartridge in accordance with one of the present inventions includes a housing, a needle and a plurality of sensible members.

An apparatus in accordance with one of the present inventions includes a cartridge with at least one sensible member and a partially implantable medical device adapted to sense the at least one sensible member.

A fluid and power cartridge in accordance with one of the present inventions includes a housing, a needle, a power source carried by the housing, and power contacts.

An apparatus in accordance with one of the present inventions includes a fluid and power cartridge and a partially implantable medical device including a percutaneous port with an interior configured to receive the fluid and power cartridge.

An apparatus in accordance with one of the present inventions includes a percutaneous port configured to receive a cartridge, an implantable operative portion including a fluid transfer device with an inlet and an outlet, and a delivery/manifold tube operably connected to the inlet and the outlet.

An apparatus in accordance with one of the present inventions includes a manifold portion, with first and second fluid lumens and a lumen-free portion that prevents direct flow from the first fluid lumen to the second fluid lumen, and a delivery portion including a delivery lumen that is operably connected to the second fluid lumen.

A method in accordance with one of the present inventions includes the steps of delivering a first substance to a location within a patient's body with a partially implantable medical device and delivering a second substance to the patient with a device other than a partially implantable medical device.

A method in accordance with one of the present inventions includes the steps of providing a patient with a first medication stored in a cartridge that is configured to be received by a partially implanted medical device and providing the patient with a second medication in an inhalable form.

A method in accordance with one of the present inventions includes the steps of supplying a patient with an insulin cartridge that stores liquid insulin and is configured to be received by a partially implantable medical device and supplying the patient with insulin in an inhalable form.

BRIEF DESCRIPTION OF THE DRAWINGS

Detailed description of exemplary embodiments will be made with reference to the accompanying drawings.

FIG. 1 is a block diagram in accordance with one embodiment of a present invention.

FIG. 2 is a perspective view of a medical device in accordance with one embodiment of a present invention.

FIG. 3 is another perspective view of the medical device illustrated in FIG. 2.

FIG. 28 is a section view of a portion of the medical device illustrated in FIGS. 2 and 3.

FIG. 29 is a perspective view of a delivery/manifold tube in accordance with one embodiment of a present invention.

FIG. 39 is a side of a medical device in accordance with one embodiment of a present invention.

FIG. 40 is plan view of a portion of the medical device illustrated in FIG. 39.

FIG. 41 is plan view of a portion of the medical device illustrated in FIG. 39.

FIG. 42 is section view taken along line 42-42 in FIG. 39.

FIG. 43 is a side of a medical device in accordance with one embodiment of a present invention.

DETAILED DESCRIPTION OF EXEMPLARY EMBODIMENTS

Figures 4, 4A:
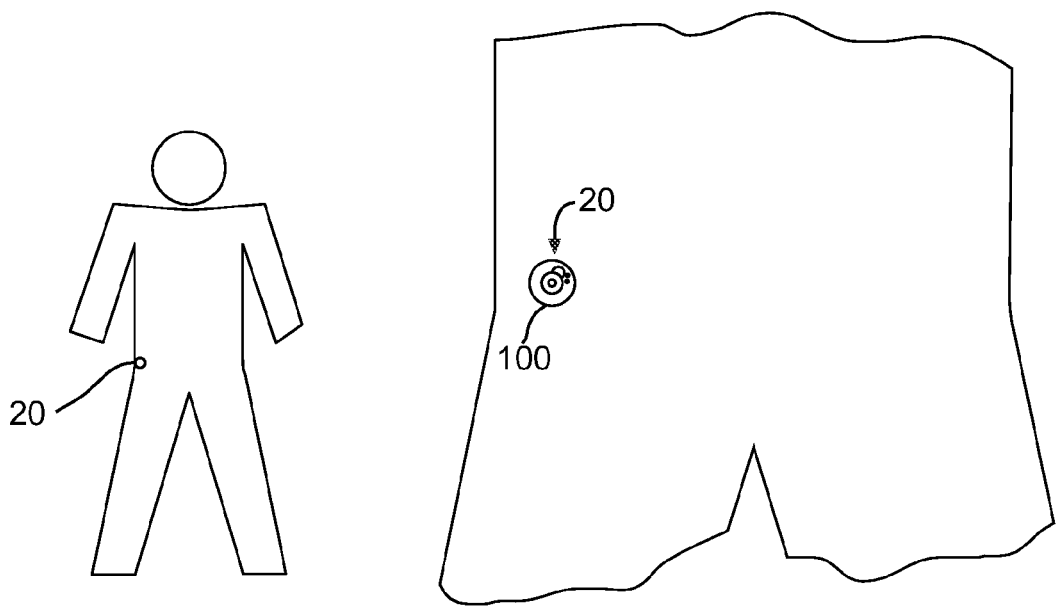
FIG. 4 is an elevation view showing the medical device illustrated in FIGS. 2 and 3 implanted in a patient with the cartridge in place.
FIG. 4A is an enlarged elevation view showing the medical device illustrated in FIGS. 2 and 3 implanted in a patient with the cartridge removed.

The following is a detailed description of the best presently known modes of carrying out the inventions. This description is not to be taken in a limiting sense, but is made merely for the purpose of illustrating the general principles of the inventions.

The detailed description of the preferred embodiments is organized as follows:

I. Introduction and Overview
II. Exemplary Percutaneous Port
III. Exemplary Replaceable Cartridge
IV. Exemplary Implantable Operative Portion
V. Exemplary Delivery/Manifold Tube
VI. Exemplary Control Methodologies
VII. Exemplary Internal Port
VIII. Additional Exemplary Implementations
IX. Exemplary Treatment Methodologies The section titles and overall organization of the present detailed description are for the purpose of convenience only and are not intended to limit the present inventions.

I. Introduction and Overview

The present inventions are generally directed to partially implantable medical devices, i.e. medical devices that are configured such that, after implantation, a portion of each device will extend completely through the epidermis. The present medical devices may be used for therapeutic and/or diagnostic purposes such as, for example, delivering a drug to a patient. As illustrated for example in FIG. 1, a medical device 10 in accordance with at least some of the inventions disclosed herein includes a percutaneous port 12, a replaceable cartridge 14 that is configured to be received by the percutaneous port, and an implantable operative portion 16.

The percutaneous port 12 extends through the epidermis from a location within the body (e.g. a location within the abdomen) and, accordingly, allows a patient or physician to access various portions of the medical device 10 from outside the body. Access is attained without further incision into the patient or the use of other devices and methods to facilitate percutaneous access. By way of comparison, to refill many fully implantable infusion devices with a drug or other infusible substance, a physician must push a needle through the patient's skin and into the abdomen in order to access the refill port on the infusion device. An implanted battery would ultimately be depleted and the device would likely be surgically replaced unless the battery was rechargeable. Also, a surgical procedure may be required to replace a blocked delivery catheter on a fully implantable infusion device.

The present percutaneous port 12, on the other hand, allows the patient or physician to easily remove and/or replace the replaceable cartridge 14 from the outside of the patient's body. In at least some implementations, the percutaneous port 12 also allows the patient or physician to remove and replace certain aspects of the percutaneous port itself, remove and replace certain aspects of the implantable operative portion 16 through the percutaneous port, remove and replace some other device that may be used in combination with the medical device 10 (e.g. a battery or other power supply) and/or recharge a rechargeable battery. There are a variety of advantages associated with such percutaneous access. For example, in some conventional fully implantable infusion devices, the battery must last many years and, accordingly, is relatively large (e.g. as much as about one-fourth of the total device volume). The ability to replace and/or recharge the battery(s) by way of the present percutaneous port 12 facilitates the use of smaller batteries, which results in a smaller medical device. Moreover, in at least some implementations, the tube that delivers fluid to the target body region may be removed and replaced by way of the percutaneous port 12, thereby eliminating the need for a surgical procedure should the tube become blocked.

The percutaneous port 12 may be configured so as to encourage tissue ingrowth into a portion thereof. Such tissue ingrowth creates an infection resistant barrier around the percutaneous port 12. The percutaneous port 12 may be carried by the implantable operative portion 16. The percutaneous port 12 may, alternatively, be operatively connected to the implantable operative portion 16 by a suitable structure such as, in the exemplary context of an implantable infusion device, a fluid tube.

In the exemplary embodiment, the replaceable cartridge 14 supplies the implantable operative portion 16 with something that is transferred to the patient and/or is otherwise consumed by the implantable operative portion. In the exemplary context of a partially implantable infusion device, the replaceable cartridge 14 may function as the medical device reservoir and be used to provide the drug or other infusible substance that is supplied to the patient by the implantable operative portion 16. There are a variety of advantages associated with a percutaneous port and cartridge-based reservoir. For example, the reservoir may occupy as much as two-thirds of the total volume of a conventional fully implantable infusion device. The large reservoir is dictated by the difficulties associated with the refill of a fully implantable infusion device, e.g. it may require a visit to a physician for a percutaneous needle-based refilling procedure, and the desirability of limiting the frequency of such procedures. In the exemplary context of high concentration insulin delivery, the conventional reservoir is configured to carry a three to six month supply. The volume of the replaceable cartridge 14 may, on the other hand, be considerably less. In the exemplary context of high concentration insulin delivery, a cartridge could be configured to store a seven day supply, which results in about an approximately 90% volumetric reduction in the overall medical device as compared to a device that stores a 3 month supply.

The replaceable cartridge 14 may, in some implementations, also be configured to supply power to the implantable operative portion 16 by way of the percutaneous port 12, thereby obviating the issues associated with a more permanent battery.

The replaceable cartridge 14 may also be used to perform a variety of other functions, such as providing a direct user interface to the implantable operative portion 16, either alone or in combination with other structures. For example, the user or physician may control certain aspects of the implantable operative portion 16 (e.g. delivery rate) by rotating the cartridge 14 relative to the percutaneous port 12. There are a variety of advantages associated with such a user interface. For example, conventional fully implantable infusion devices are generally controlled by way of telemetric communication from an external remote control. The additional expense associated with this communication method notwithstanding, patients are unable to interface with their fully implanted infusion devices should they find themselves without their remote controls.

The implantable operative portion 16 performs the therapeutic and/or diagnostic functions associated with the medical device 10 and, as used herein, an "implantable" operative portion is an operative portion that is sized, shaped and otherwise constructed (e.g. sealed) such that it can be entirely carried within the patient's body. In the exemplary context of a partially implantable infusion device, the implantable operative portion may include, among other things, a fluid transfer device (e.g. a pump and valve arrangement) and control apparatus.

One example of a medical device which incorporates many of the present inventions is the medical device 20 illustrated in FIGS. 2 and 3. The illustrated example includes a percutaneous port 100, a replaceable cartridge 200, and an implantable operative portion 300. A replaceable delivery/manifold tube 400 may be provided in some implementations. The particulars of the exemplary medical device 20 are discussed in Sections II-VI below.

Figure 5:
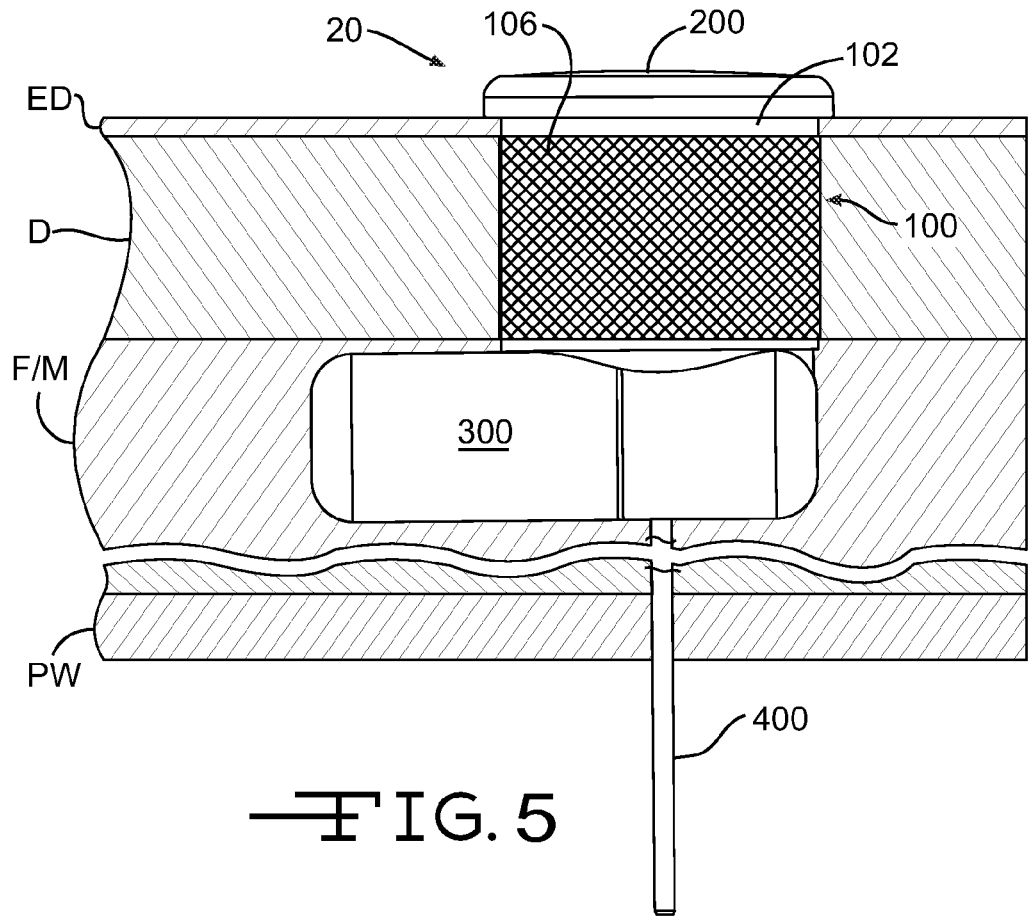
FIG. 5 is a side, partial section view of the medical device illustrated in FIGS. 2 and 3 implanted in a patient with the cartridge in place.

Turning to FIGS. 4, 4A and 5, the medical device 20 may, for example, be implanted into the abdomen of a patient such that the replaceable cartridge 200 will be adjacent to exterior surface of the skin and available for removal and/or other manipulation. One suitable location is the front side of the abdomen. For cosmetic purposes, the exterior color of the cartridge 200 (or at least the visible surface thereof) may be chosen to match the patient's skin color. Alternatively, the visible surface of the cartridge may be configured to resemble jewelry (such as that sometimes carried by body piercings), may resemble a tattoo, or may resemble some other decorative instrumentality. The replaceable cartridge 200 may be removed (FIG. 4A) from the percutaneous port 100, replaced, or otherwise manipulated, without disturbing the implantable operative portion 300. The percutaneous port 100 may also, for example, be used to obtain physical or electronic access to certain aspects of the port, and/or to replace the delivery/manifold tube 400, when there is no cartridge 200 in the port.

In the exemplary context of insulin delivery, the implantable operative portion 300 may be located subcutaneously within fat and/or muscle F/M, but outside the peritoneal cavity, and the delivery portion of delivery/manifold tube 400 may extend through the peritoneal wall PW and into the peritoneal cavity, as illustrated in FIG. 5. There are variety of advantages associated with delivering insulin to the peritoneal cavity. For example, it is less likely that there will be tissue build-up at the outlet end of a delivery tube that is located in the peritoneum, as compared to the outlet end of a delivery tube that is located subcutaneously. Delivery of insulin into the peritoneal cavity, as opposed to subcutaneous delivery, results in better delivery kinetics, eliminates the depot effect, is more natural (a healthy pancreas delivers insulin to the peritoneal cavity), and the insulin peaks almost twice as fast as for subcutaneous injections of insulin.

It should also be noted that, depending on the therapy, the present partially implantable medical devices may be used for subcutaneous delivery, venous delivery, intranodal delivery, and delivery to any organ.

II. Exemplary Percutaneous Port

Referring first to FIGS. 2, 3 and 5, the exemplary percutaneous port 100 includes a tubular wall 102 with a rounded rim 104 and a layer of porous material 106. The rounded rim 104, which may be located adjacent to the epidermal surface when the medical device 20 is implanted into the patient, strengthens the tubular wall 102 and eliminates what might otherwise be a sharp edge that is uncomfortable to the touch. The layer of porous material 106, which may at a minimum be located just below the patients epidermis ED and in contact with the dermis D (FIG. 5), is configured to encourage tissue ingrowth that creates an infection resistant barrier around the tubular wall 102 after implantation. The layer of porous material 106 extends around the entire circumference of the tubular wall 102 (as shown) and may extend from one longitudinal end of the tubular wall to the other, or over only a portion of the tubular wall below the rim 104, or over a portion of the tubular wall adjacent to the implantable operative portion 300, or over a portion of the tubular wall therebetween. In certain exemplary implementations, the layer of porous material 106 may be a mesh of intersecting fibers of any suitable biocompatible material, such as a biocompatible metal (e.g., titanium, nitinol, stainless steel, gold, or platinum) or a biocompatible polymeric material (e.g., polyolefins, TEFLON polytetrafluoroethylene (PTFE), nylon, DACRON polyester, or silicone). The mesh may be formed by cross-winding the fibers in multiple layers to define a porosity conducive to promoting tissue ingrowth (e.g., pore sizes within a range of 50 to 200 microns and having a porosity of 60 to 95%). The infection resistant barrier may be enhanced by incorporating antimicrobial and/or anti-inflammatory constituents into or beyond the layer of porous material 106. Additional details concerning such porous material layers may be found in U.S. Patent Pub. Nos. 2004/0204686, 2007/0112334 and 2007/0149949, each of which is incorporated herein by reference.

The exemplary percutaneous port 100 is circular in cross-section in order to accommodate the cylindrical cartridge 200. It should be noted, however, that the present percutaneous port may have cross-sectional shapes other than circular in order to, for example, accommodate cartridges that are oval, square, rectangular, or otherwise.

Figure 10:
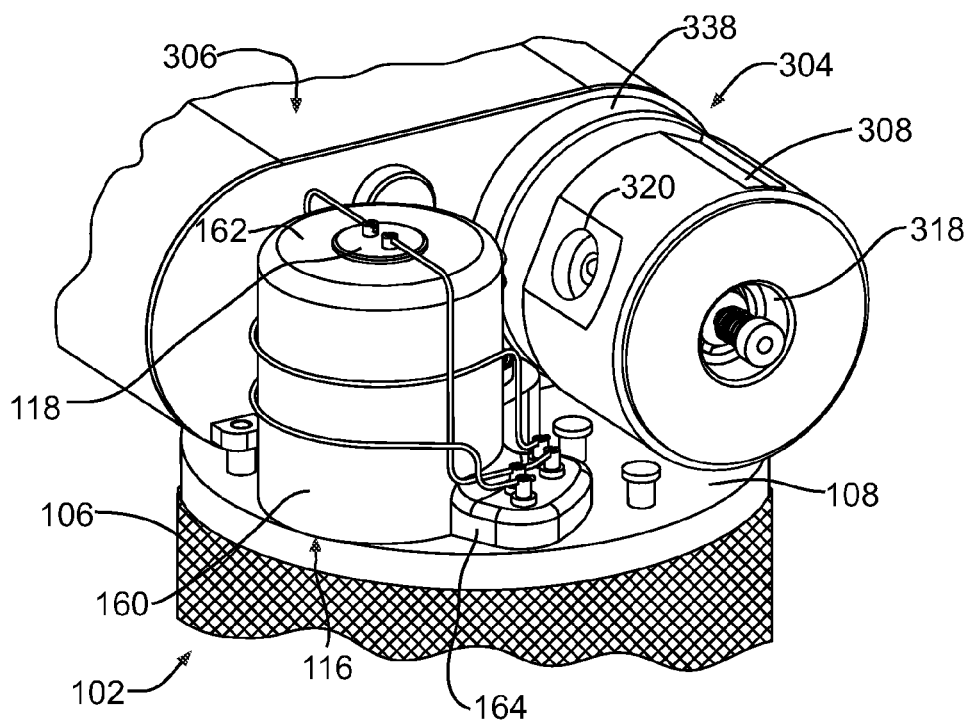
FIG. 10 is a perspective view of a portion of the medical device illustrated in FIGS. 2 and 3.
Figures 11, 12:
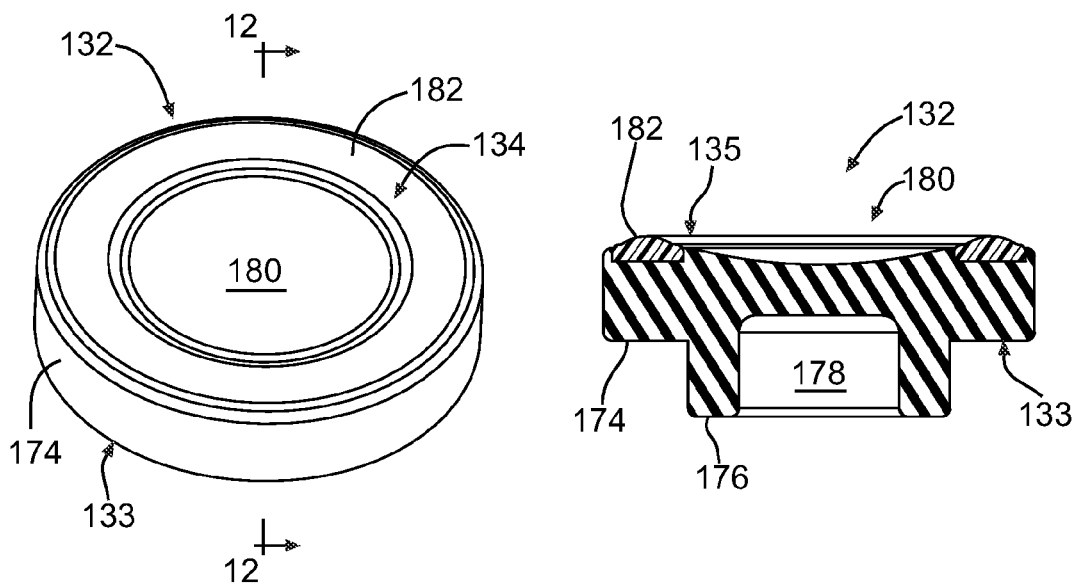
FIG. 11 is a perspective view of a septum in accordance with one embodiment of a present invention.
FIG. 12 is a section view taken along line 12-12 in FIG. 11.

Turning to FIGS. 6-9, the exemplary percutaneous port 100 also includes an end wall 108. The tubular wall 102 and the end wall 108 together define an interior cartridge receiving region 110 and, put another way, the tubular wall and the surface of the end wall that contacts the cartridge together perform the function of receiving and holding the cartridge 200 (see also FIGS. 5, 7, 16 and 28). The end wall 108 includes a plurality of apertures and indentations that are associated with various structures and functions that are related to the percutaneous port 100. For example, the end wall 108 includes an aperture 112 that allows one or more batteries 114 to be inserted into, and removed from, a battery case 116, which has a positive battery contact 118. The battery case 116 is discussed in greater detail below with reference to FIGS. 9 and 10. The end wall 108 also includes a pair of apertures 120 and 122 for control sensors 124 and 126. The control sensors 124 and 126, which are discussed in greater detail below with reference to FIG. 9 and in Section VI, are used to sense rotation of the cartridge 200 relative to the port 100. In the illustrated implementation, the control sensors are at the surface or extend slightly above the surface of the end wall 108. An aperture 128 is provided for the replaceable delivery/manifold tube 400, which is discussed in greater detail in Section V below, while an aperture 130 is provided for a septum 132 that is located over the delivery/manifold tube. The septum 132, which is discussed in greater detail below with reference to FIGS. 11 and 12, is the structure through which fluid from the cartridge 200 is delivered to the implantable operative portion 300 (by way of the delivery/manifold tube 400). To that end, the exemplary cartridge 200 includes a delivery needle 204 (FIGS. 13-15) and the septum 132 is configured to allow passage of the needle. The septum 132 also functions as a seal, both when the needle 204 is extending therethrough and after the needle has been removed, to prevent contaminants within the interior cartridge receiving region 110 of the percutaneous port from entering the delivery/manifold tube 400. The seal also prevents infusible substance within the delivery/manifold tube 400 leaking into the interior cartridge receiving region 110 of the percutaneous port 100.

It is anticipated that the batteries 114 may need replacement, that the septum 132 may fail in response to the repeated needle puncturing associated with cartridge replacement, and/or that the delivery/manifold tube 400 may become blocked or damaged. As such, the batteries 114, septum 132 and delivery/manifold tube 400 are removable and replaceable and may be removed and replaced by way of the percutaneous port 100. To that end, the wall that defines the aperture 130 in the illustrated embodiment is also configured to mate with a releasable retainer 134 that holds the batteries 114, the septum 132 and the delivery/manifold tube 400 in place. The exemplary retainer 134 includes a flat retainer disk 136 and a post 138. The end wall 108 includes an indentation 140 that is substantially the same diameter and thickness as the flat retainer disk 136 and, accordingly, the end wall and flat retainer disk will be essentially flush when the retainer 134 is in the locked position illustrated in FIG. 7. In the illustrated embodiment, the exterior surface of the post 138 includes threads 142, while the wall that defines the aperture 130 includes threads 144 which are configured to mate with the post threads. The retainer 134 may be secured to the end wall 108 by inserting the post 138 into the aperture 130, and then rotating the retainer until the flat retainer disk 136 engages indentation 140. The flat retainer disk 136, which also engages the adjacent battery 114 when the retainer 134 is in the locked position (FIG. 7), functions as the negative battery contact. The electrical paths from the positive and negative battery contacts are discussed in Section IV below.

A lumen 146 extends through the retainer 134 in the exemplary implementation. The purpose of the lumen 146 is twofold. The lumen 146 provides a passageway, which leads to the septum 132 and to the delivery/manifold tube 400, for the cartridge needle 204 (FIG. 28). The lumen 146 is also configured to receive a tool (not shown) that may be used to rotate the retainer 134. In the illustrated embodiment, the lumen 146 is hexagonally-shaped and, accordingly, is configured to receive a tool such as an Allen wrench that is correspondingly hexagonally-shaped. Other suitable lumen/tool configurations include, but are not limited to square (or "Robertson"), triple square and star shapes.

It should also be noted here that the inner surface of the exemplary tubular wall 102 may be provided with an indentation 148 that is configured to mate with a sealing ring 216 (FIG. 16) on the cartridge 200, as is discussed in Section III below. Additionally, and referring to FIG. 8, the side of the end wall 108 opposite the interior cartridge receiving region 110 includes a ring 150 onto which the battery case 116 (FIGS. 9 and 10) is mounted, a base member 152 in which the apertures 128 and 130 (FIG. 6) are formed, a ring 154 on which the delivery/manifold tube receiver 366 (FIGS. 23 and 24) is mounted, one or more anchors 156, and a pin 158. The ring 154, anchors 156 and pin 158 are discussed in greater detail below in Section IV below. An adhesive may be used to secure the battery case 116 to the ring 150.

Figure 9:
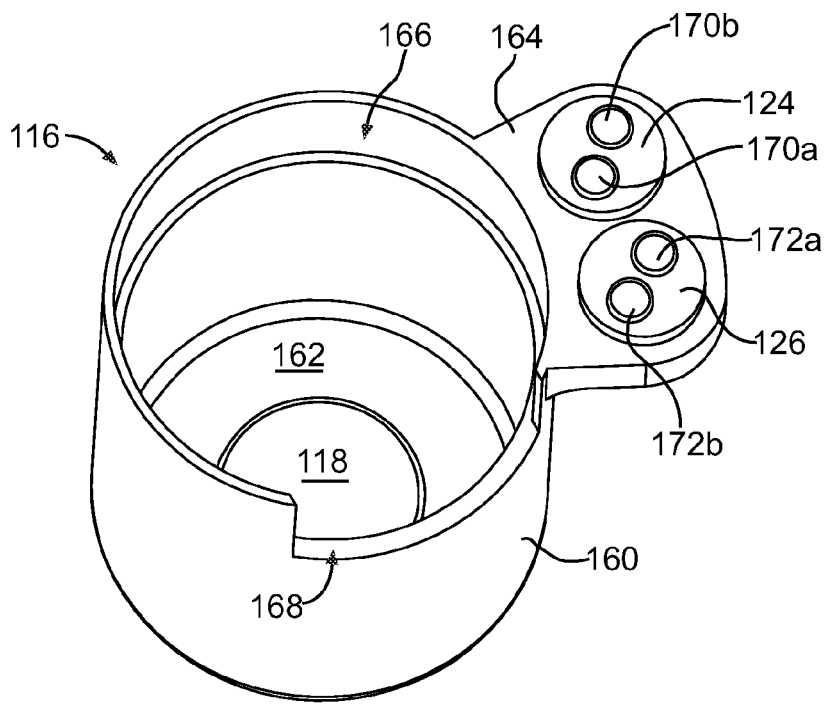
FIG. 9 is a perspective view of a battery case in accordance with one embodiment of a present invention.

As illustrated in FIG. 9, the exemplary battery case 116 includes a cylindrical wall 160, an end wall 162 that carries the battery positive contact 118, and a flange 164 that carries the control sensors 124 and 126. The cylindrical wall 160 has indentations 166 and 168 to accommodate the ring 150 and base member 152 and allow the battery case 116 to be mounted on the percutaneous port end wall 108 in the manner illustrated in FIG. 10. Suitable materials for the battery case 116 include, but are not limited to, polyethylene, polycarbonate, PEEK, TEFLON PTFE, epoxy and others. The present medical devices are not limited to any particular type of control sensor. The type of control sensor will depend, at least in part, upon the type of sensible members carried by the cartridge 200. In the illustrated embodiment, the circumferentially spaced control sensors 124 and 126 respectively consist of pairs of electrical contacts ("contact pairs") 170a/170b and 172a/172b, and the electrical contacts within each contact pair are substantially circumferentially aligned (note FIG. 7).

Turning to FIGS. 11 and 12, the exemplary replaceable septum 132 includes seal member 133 and an annular low friction retainer engagement member 135. The seal member 133 has a relatively wide portion 174, a relatively narrow portion 176 and a hollow region 178. The relatively wide portion 174 is configured to fit within the aperture 130 and rest on the base member 152 (note FIG. 6), creating a seal. The relatively narrow portion 176 is configured to fit within the aperture 128 and rest on the delivery/manifold tube 400. The retainer engagement member 135, which is engaged by the lock post 138 (FIG. 6) and is carried by the relatively wide portion 174, defines an aperture 180 through which the cartridge needle 204 may pass, and includes a curved surface 182. The low friction lock engagement member 135 allows the lock 134 to be rotated without rotating, or rotationally deforming, the replaceable septum 132, while compressing the rim of the septum assembly at 133 to effect the seal. Suitable materials for the seal member 133 include, but are not limited to, resilient materials such as silicone rubber and polyurethane, while the low friction member 135 may be formed from materials, such as TEFLON PTFE, a polished metal (e.g. titanium or stainless steel), or a film (e.g. TEFLON PTFE, nylon or polycarbonate) that is adhered to the seal member 133, which have a lower coefficient of friction than the seal member. In other implementations, the retainer engagement member may simply be in the form of a non-stick coating, such as a coating of a TEFLON PTFE or a low friction polymer, on the seal member 133. It should also be noted that the septum is not limited to the illustrated shape with a narrow portion and a wide portion and could, for example, simply be disk-shaped.

There are a variety of advantages associated with the present percutaneous port 100. By way of example, but not limitation, the percutaneous port 100 may be used to receive a replaceable cartridge (e.g. cartridge 200) that is used to store the drug or other infusible substance that is supplied to the patient by the implantable operative portion 300. As noted above, providing the infusible substance in this manner is more convenient and greatly reduces the overall size of the medical device 20 as compared to fully implantable infusion devices. The percutaneous port 100 may also be used for maintenance. To that end, and as noted above, the percutaneous port allows the batteries 114, the septum 132 and the delivery/manifold tube 400 to be removed and replaced. In addition to eliminating the need for surgical procedures to replace the delivery tube, the ability to replace the batteries 114 facilitates the use of a smaller power source than is required for a fully implantable infusion device that must remain implanted for many years. Other advantages, which are associated with the sensing features of the percutaneous port 100, are discussed in Section VI below.

III. Exemplary Replaceable Cartridge

Figure 14:
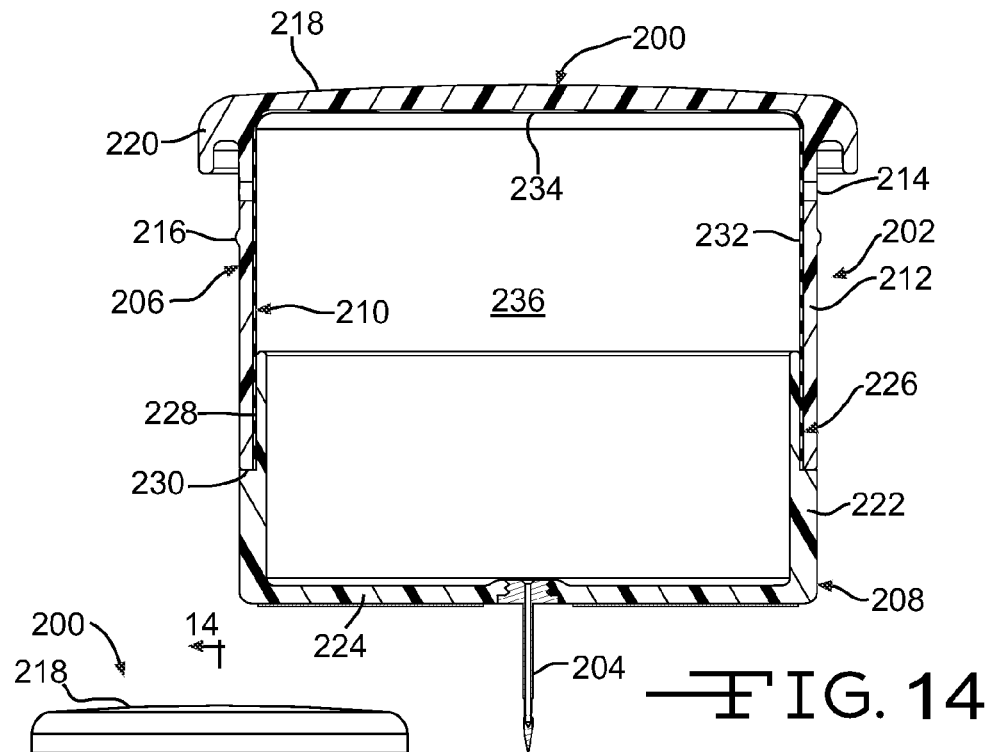
FIG. 14 is a section view taken along line 14-14 in FIG. 13.
Figure 13:
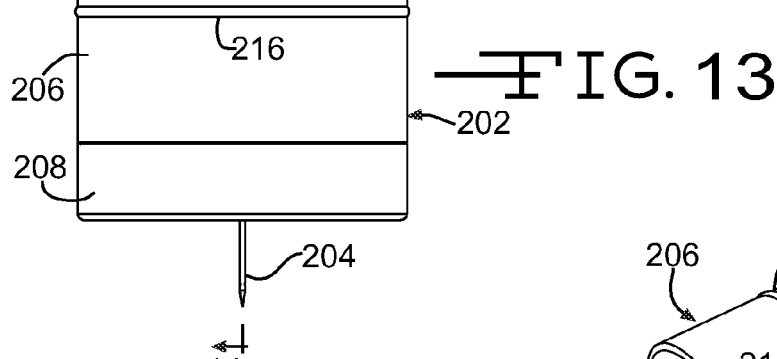
FIG. 13 is an elevation view of a cartridge in accordance with one embodiment of a present invention.
Figure 15:
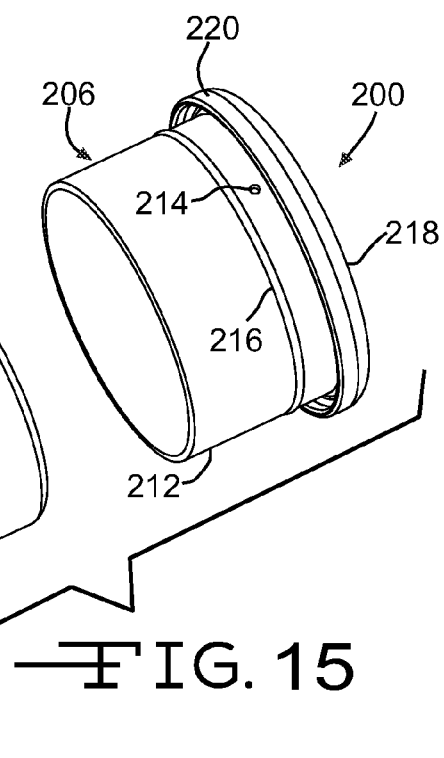
FIG. 15 is an exploded perspective view the cartridge illustrated in FIG. 13.

As illustrated in FIGS. 13-15, the exemplary replaceable cartridge 200 includes a housing 202, which stores the infusible substance, and a needle 204. Although the present cartridges are not limited to any particular housing structure, the exemplary housing 202 has first and second housing members 206 and 208 and an internal bladder 210.

Figure 16:
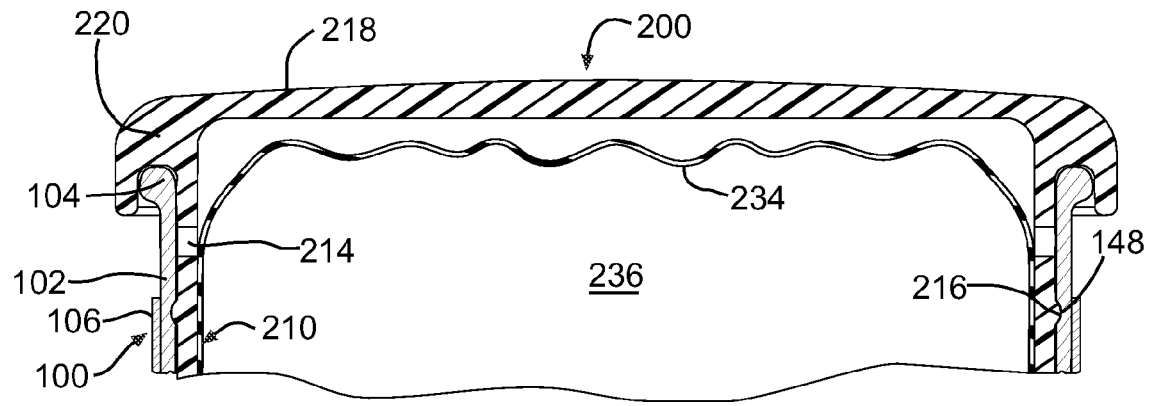
FIG. 16 is an enlarged view of a portion of FIG. 14.

The first housing member 206 in the exemplary replaceable cartridge 200 includes a cylindrical wall 212, with one or more air holes 214 and a sealing ring 216, and an end wall 218 that is sized such that it extends radially beyond the percutaneous port rounded rim 104 (FIGS. 2, 3 and 16). For example, the end wall 218 may have a flange 220 that rests on and curls around the rim 104 when the cartridge 200 is fully inserted into the percutaneous port 100 (FIG. 16), or may simply have a flat flange that rests on the rim (discussed below with reference to FIG. 44). The second housing member 208 includes a cylindrical wall 222 and an end wall 224. The cylindrical wall 222 includes an indentation 226, with a longitudinally extending surface 228 and a radially extending surface 230, that is configured to receive a portion of the first housing member cylindrical wall 212 with a portion of the internal bladder 210 therebetween. The end wall 224 may be flat (as shown), convex, or concave. Suitable materials for the housing members 206 and 208 include, but are not limited to, plastics such as polyethylene or PEEK, or other polymers.

The internal bladder 210 in the exemplary embodiment illustrated in FIGS. 13-15 is formed from a flexible film and includes a cylindrical side wall 232 and an end wall 234. There are also no folds in the side and end walls 232 and 234. The side wall 232 is located within the indentation 226, abuts the radially extending surface 230 and is compressed between the associated portions of the cylindrical walls 212 and 222. So configured and arranged, the internal bladder 210 and the second housing member 208 together define a fluid storage volume 236 that, when filled with fluid (FIG. 15), is essentially equal to the internal volume of the housing 202. The configuration of the internal bladder 210 in the illustrated embodiment is such that the bladder is not stretched, and does not exert a positive pressure on the fluid, when the cartridge 200 is full. The internal bladder 210 will collapse (FIG. 16) as fluid is drawn from the cartridge 200 and air enters the volume that is formed between the housing member 206 and the internal bladder 210 by way of the air holes 214. Suitable materials for the internal bladder include, but are not limited to silicone or butyl rubber.

It should be noted here that the present cartridges are not limited to the illustrated internal bladder embodiment. Other devices may be used alone, or in combination with the housing members 206 and 208, to define the fluid storage volume. By way of example, but not limitation, such devices may include plungers that slide within the space defined by the housing members, flexible bellows, and other suitable structures. Also, another suitable bladder is a balloon without a defined shape.

Referring to FIG. 16, the flange 220 on the cartridge housing 202 will engage the percutaneous port rounded rim 104 to minimize the inflow of water, but not create an airtight seal, when the cartridge 200 is fully inserted into the percutaneous port 100. Instead, in the illustrated embodiment, the exemplary seal is air permeable so that air can reach the air holes 214. The seal resists the inflow of water under normal conditions, but will not prevent rotation of the cartridge 200 relative to the percutaneous port 100 (note the discussion in Section VI below). So configured, the exemplary seal will be tight enough to prevent water from entering the percutaneous port 100 during everyday water-related activities such as showering, but not tight enough to prevent water from entering the percutaneous port during swimming and diving. The sealing ring 216 on the housing 202 will also mate with the indentation 148 in the tubular wall 102 when the cartridge 200 is fully inserted into the percutaneous port 100. In addition to providing a more effective seal, the mechanical interference associated with the indentation 148 and ring 216 will prevent the cartridge 200 being unintentionally dislodged from the percutaneous port 100 during normal activities. The indentation and ring arrangement results in a small gap between the inner surface of the percutaneous port tubular wall 102 and the outer surface of the cartridge housing 202, which facilitates air flow into the holes 214. Alternatively, or in addition, any suitable mechanical lock (e.g. a click lock) may be provided to provide a retention to keep the cartridge 200 in the port 100. A magnetic locking arrangement is another alternative.

For swimming, diving and other activities that could result in leakage or dislodgement of the cartridge 200, the cartridge may be removed and replaced by a stopper (e.g. a rubber stopper) that is configured to create a tighter seal than the cartridge. Such an arrangement may, for example, be useful in those instances where the batteries 114 would be damaged if immersed in water. The removal time would depend upon the application of the medical device. In the exemplary context of insulin delivery, the removal time could be as long as a couple of hours without danger. Tape seals, such as those sold by Smith & Nephew, may be secured to the skin and positioned over the top of the cartridge 200 or simply positioned within the port 100 over the battery 114, to protect against water intrusion.

Figure 17:
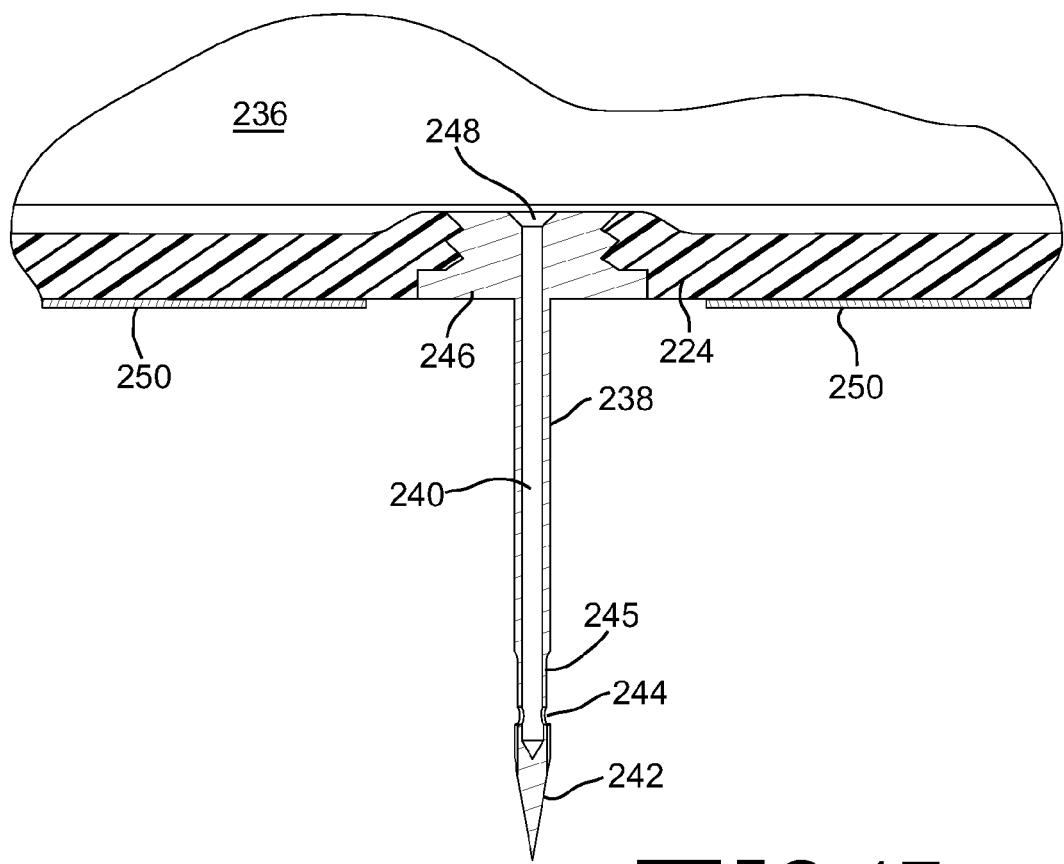
FIG. 17 is an enlarged view of a portion of FIG. 14.

Turning to the cartridge needle, the needle 204 may be carried by the end wall 224 and, in the illustrated embodiment, the needle is located at the center of the end wall and extends along longitudinal axis of the cartridge 200. Although the present cartridges may include any suitable needle configuration, the exemplary needle 204 is a non-coring needle that reduces the likelihood that it will damage the septum 132 when the cartridge is inserted into and removed from the percutaneous port 100. To that end, and referring to FIG. 17, the exemplary needle 204 includes an elongated tubular body 238, with an internal lumen 240, and a sharpened end portion 242. One or more apertures 244 pass through the tubular body 238 to the internal lumen 240. The needle 204 may be configured such that the sharp edges associated with the apertures 244 are not located on the sharpened end portion 242 and, instead, are located inwardly from the overall outer perimeter of the tubular body 238, which reduces the likelihood that the needle 204 will damage the septum 132. The apertures 244 in the illustrated embodiment are located within longitudinally extending indentations 245 that have rounded edges. The exemplary needle 204 also includes a base 246 that is mounted in the end wall 224. The internal lumen 240 extends through the base 246 and defines a needle inlet 248 that is located within the fluid storage volume 236.

The size of the fluid storage volume 236 will, of course, depend on the intended application. In the exemplary context of insulin delivery, the cartridge 200 may be configured such that it can store one week's worth of highly concentrated insulin that is to be delivered at a relatively high delivery rate. For example, if the maximum daily basal dosage is 100 units/day, a fluid storage volume of 1.8 cc would be sufficient to store a week's supply of an insulin that has a 400 units/cc concentration (e.g. Sanofi-Aventis U400). Such a volume could, for example, be achieved with a cartridge that has an internal diameter of about 14 mm and an internal height of about 12 mm. The outer diameter of housing 202 would be about 15 mm, the exterior height of the housing would be about 12 mm (excluding the end wall 218), and the diameter of the end wall 218 (including the flange 220) could be about 16-17 mm in such a cartridge. Additionally, with respect to other exemplary applications, the size of the fluid storage volume may range from 0.1 cc to 20 cc in applications such as for pain therapy with morphine.

Referring to FIG. 15, the exemplary cartridge 200 also includes one or more sensible members 250 that are sensed by the sensors 124 and 126. Sensing of the sensible members 250 is used to identify rotation of the cartridge 200 relative to the percutaneous port 100 in the manner described in Section VI below. The sensible members 250 may be located on the exterior of the second housing member end wall 224 (as shown), on the exterior of the cylindrical walls 212 and 222, on the exterior of the first housing member end wall 218, completely or partially embedded within one or more of any of the end and cylindrical walls, or even within the internal volume of the cartridge, depending upon the type of sensible member employed, the location of the associated sensor(s) and the manner in which the sensible member(s) and sensor(s) interact.

In the illustrated embodiment, the sensible members 250 are circumferentially-spaced electrically conductive pads that are separated by non-conductive regions 251. The configuration of the percutaneous port 100 is such that a conductive pad will be in contact with the contacts 170a/170b and 172a/172b when a portion of that conductive pad is circumferentially aligned therewith. The above-described indentation 148 and ring 216, and there positioning relative to the remainders of the percutaneous port 100 and cartridge 200, may be used to apply a slight positive pressure which insure that the sensible members 250 will make contact with the contacts 170a/170b and 172a/172b when the sensible members and contacts are aligned.

Suitable examples of electrically conductive materials for the pads include, but are not limited to, stainless steel, copper, aluminum, silver, gold and nickel. The conductive pads may be formed on the associated wall (e.g. end wall 224) through the use of any suitable technique. By way of example, but not limitation, the conductive pads may be formed by electroplating or insertion molding. Alternatively, the associated wall (e.g. end wall 224) may be formed from (or coated with) conductive material and those portions of the conductive material that are not within a sensible member may be coated with a non-conductive material. The conductive pads may also be printed onto a sheet of plastic that is then adhered to the associated wall (e.g. end wall 224). Conductive material may, alternatively, be printed directly onto the associated wall (e.g. end wall 224). Another alternative is to secure a precut metal sheet to the associated wall (e.g. end wall 224) and then peel away the portions of the sheet that do not form the conducting pads. Similarly, a metalized film may be formed on the associated wall (e.g. end wall 224) and then etched to form the conductive pads.

The sensible members 250 are not limited to electrically conductive pads. For example, cartridges in accordance with other embodiments of at least some of the inventions may be provided with one or more protrusions, indentations, and/or other instrumentalities that can be mechanically sensed. Another exemplary alternative is one or more magnets that can sensed by, for example, a flux sensor.

Cartridges in accordance with at least some embodiments may be provided with information storage and communication devices that may be used to provide information to, and/or store information received from, the implantable operative portion 300. One example of such an information storage device is an RFID tag (not shown). The RFID tag may be used to provide the implantable operative portion 300 with programming information and other data. A cartridge with such an RFID tag may be used to program or reprogram the associated medical device, thereby obviating the need for telemetric communication between the medical device and an external programmer. The RFID tag may also be used to record data sensed by the implantable operative portion 300. Here, used cartridges could be returned to the manufacturer or the physician so that the data could be read and analyzed. Examples of such data include, but are not limited to, data from physiological sensors (e.g. glucose data) and failure mode data. The RFID tag may also be used as an electronic safety key to, for example, prevent the implantable operative portion 300 from operating when an unauthorized cartridge is inserted into the percutaneous port 100 or when no cartridge is present in the port. One example of an unauthorized cartridge would be a cartridge that stores a medication or other infusible substance other than that prescribed by the patient's physician.

IV. Exemplary Implantable Operative Portion

Referring to FIGS. 2 and 3, the implantable operative portion 300 of the exemplary medical device 20 includes a housing 302 with a fluid transfer section 304 and an electronics section 306. The fluid transfer components carried within the fluid transfer section 304 and the delivery/manifold tube 400 together transfer fluid from the replaceable cartridge 200 to a target location within the patient. The components within the electronics section 306 may include, among other things, the powered portion of the exemplary fluid transfer device 308 (FIGS. 18-21) as well as power and control circuitry. Although the housing 302 may be configured such that the fluid transfer section 304 and electronics section 306 share a common volume that is sealed relative to the patient, the housing in the illustrated embodiment is configured such that the electronics section is sealed relative to both the fluid transfer section and the patient. This aspect of the exemplary medical device 20 is discussed in greater detail below with reference to FIGS. 20 and 21.

A wide variety of fluid transfer devices may be incorporated into medical devices in accordance with at least some of the present inventions. In the illustrated embodiment, the fluid transfer device is in the form of an electromagnet pump. The present inventions are not, however, limited to electromagnet pumps and may include other types of fluid transfer devices. Such devices include, but are not limited to, other electromagnetic pumps, solenoid pumps, piezo pumps, MEMS pumps and any other mechanical or electromechanical pump. In the exemplary context of partially implantable drug delivery devices, and although the volume/stroke magnitude may be smaller or larger in certain situations, the fluid transfer devices in the exemplary embodiment will typically deliver about 0.25 microliter/stroke, but may be more or less depending on the particular fluid transfer device employed. To put 0.25 microliter/stroke into the exemplary context of delivering high concentration insulin, a basal rate of 40 strokes/hr (or 960 stokes/day) would provide a patient with about 96 units/day of insulin that has a concentration of 400 units/cc (e.g. Sanofi-Aventis U400). Additionally, although the exemplary fluid transfer device is provided with internal valves (e.g. a main check valve and a bypass valve), valves may also be provided as separate structural elements that are positioned upstream of and/or downstream from the associated fluid transfer device.

Figure 18:
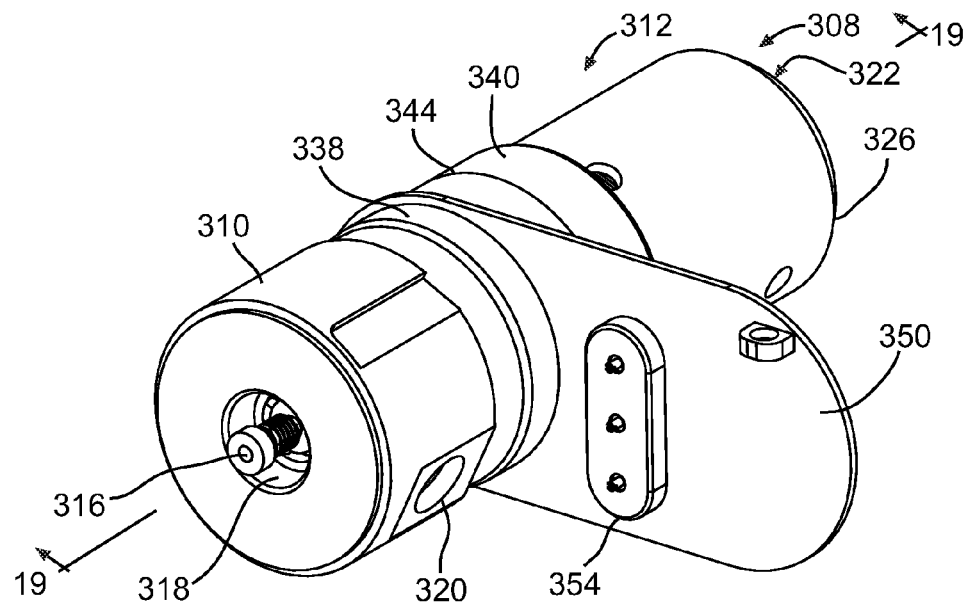
FIG. 18 is a perspective view of a fluid transfer device in accordance with one embodiment of a present invention.
Figure 19:
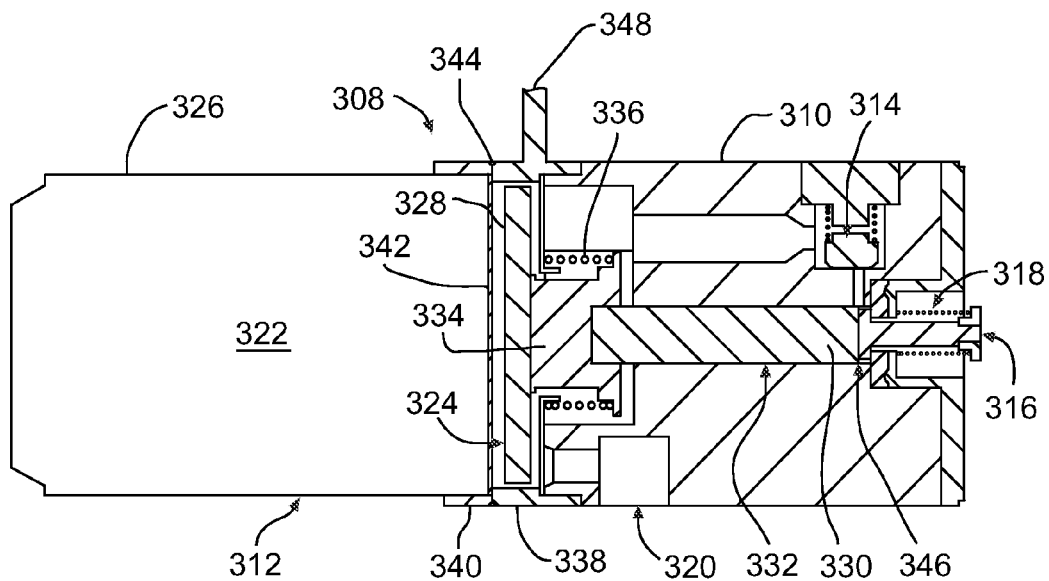
FIG. 19 is a partial section view taken along line 19-19 in FIG. 18.

As illustrated for example in FIGS. 18 and 19, the exemplary fluid transfer device is generally represented by reference numeral 308 and includes a housing 310, an electromagnet pump 312, a bypass valve 314, and a main check valve 316 that defines the fluid transfer device inlet 318. The exemplary housing 310 is a generally solid, cylindrical structure with various open regions that accommodate various structures and define fluid flow paths, as well as the fluid transfer device outlet 320. Suitable materials for the housing 310 include, but are not limited to, titanium. The exemplary electromagnet pump 312 includes an electromagnet 322 and an armature 324. The electromagnet 322, which is carried within in a case 326, includes a core and a coil. The armature 324 consists of a pole 328 formed from a magnetic material (e.g. magnetic steel), which is located such that it will be magnetically attracted to the electromagnet 322 when the electromagnet is actuated, and a cylindrically-shaped piston 330 that extends from the pole and through the piston bore 332 to the main check valve 316. A hub 334 secures the pole 328 to the piston 330, and a main spring 336 biases the armature 334 to the "rest" position illustrated in FIG. 19.

The housing 310 in the illustrated embodiment is secured to the electromagnet case 324 through the use of a weld ring 338 on the housing and a weld ring 340 on the electrical case. The outer diameters of the weld rings 338 and 340 are substantially equal to one another and the outer surfaces thereof are substantially flush. During assembly, the housing 310 and the electromagnet case 326 are positioned on opposite sides of a barrier 342, such as a titanium barrier, and are then secured to one another by a weld 344 (e.g. a laser weld) joining the outer surfaces of the weld rings 338 and 340. The barrier 342 hermetically isolates the recess around the armature pole 328, which is filled with fluid, as well as the other structures and lumens associated with the housing 310, from the electromagnet 322.

With respect to operation, the exemplary fluid transfer device 308 is actuated by connecting the coil in the electromagnet 322 to an energy source (e.g. capacitors that are being fired). The resulting magnetic field, which is directed through the electromagnet core and the armature pole 328, overcomes the biasing force of the main spring 336, and pulls the armature pole to the barrier 342. The armature piston 330 and hub 334 will move with armature pole 328 and compress the main spring 336. This is also the time at which fluid exits the fluid transfer device 308 by way of the outlet 320. The coil will continue to be energized for a brief time (e.g. a few milliseconds) and the main check valve 316 will briefly open and allow fluid into the pump chamber 346 that is located between the end of the (now moved) piston 330 and the main check valve. Immediately after the main check valve 316 closes, the electromagnet will then be disconnected from the energy source and the main spring 336 will drive the armature 324 back to the "rest" position illustrated in FIG. 19. The associated increase in pressure within the pump chamber 346 opens the bypass valve 314, thereby allowing fluid to flow to the recess around the armature pole 328. Additional information concerning the operation of electromagnet pump-based fluid transfer devices may be found in U.S. Pat. Nos. 6,227,818, 6,264,439, and U.S. Patent Pub. No. 2007/0269322, each of which incorporated herein by reference. Suitable electromagnet pump-based fluid transfer devices have been developed by Infusion Systems, LLC in Sylmar, Calif.

Figure 6:
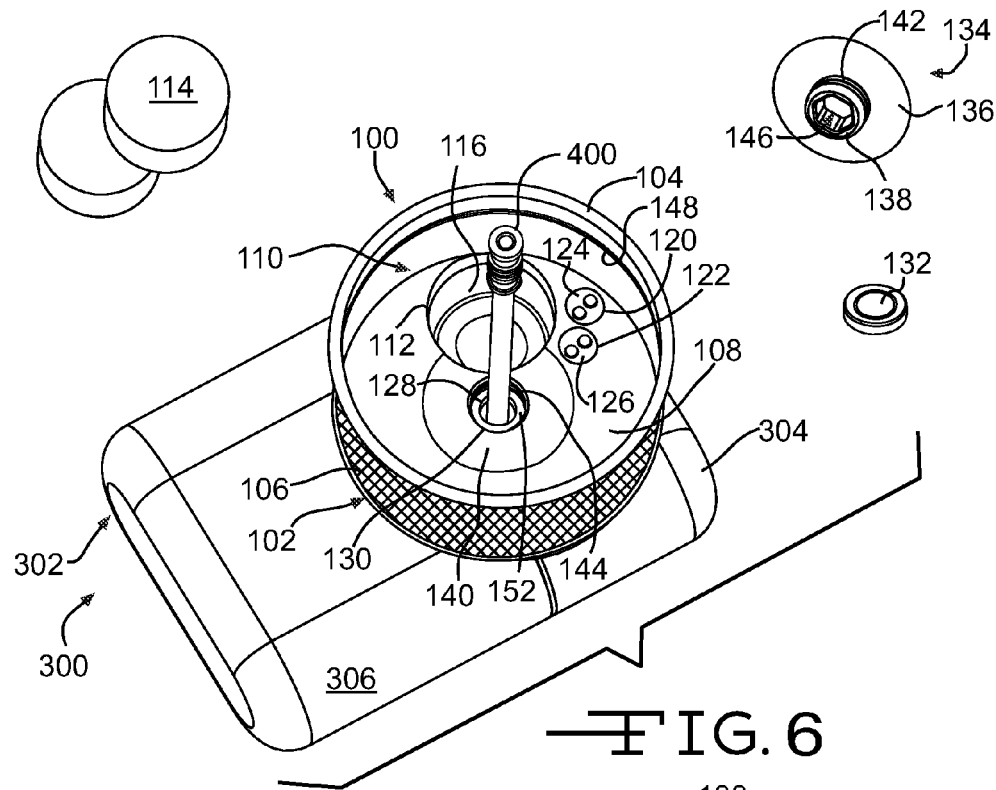
FIG. 6 is an exploded perspective view of a portion of the medical device illustrated in FIGS. 2 and 3.

As alluded to above, power for the electromagnet pump and other electrical aspects of the exemplary medical device may be provided by a pair of batteries 114 carried within the battery case 116 (FIG. 6). Suitable batteries include batteries such as Energizer silver oxide 319 batteries. A stack of three of such batteries would provide 90 VmA-hours of power, which is sufficient to power the electromagnet pump at a rate of 960 pulses/day for 4 months, and could replaced by way of the percutaneous port during visits to the physician.

Figure 7:
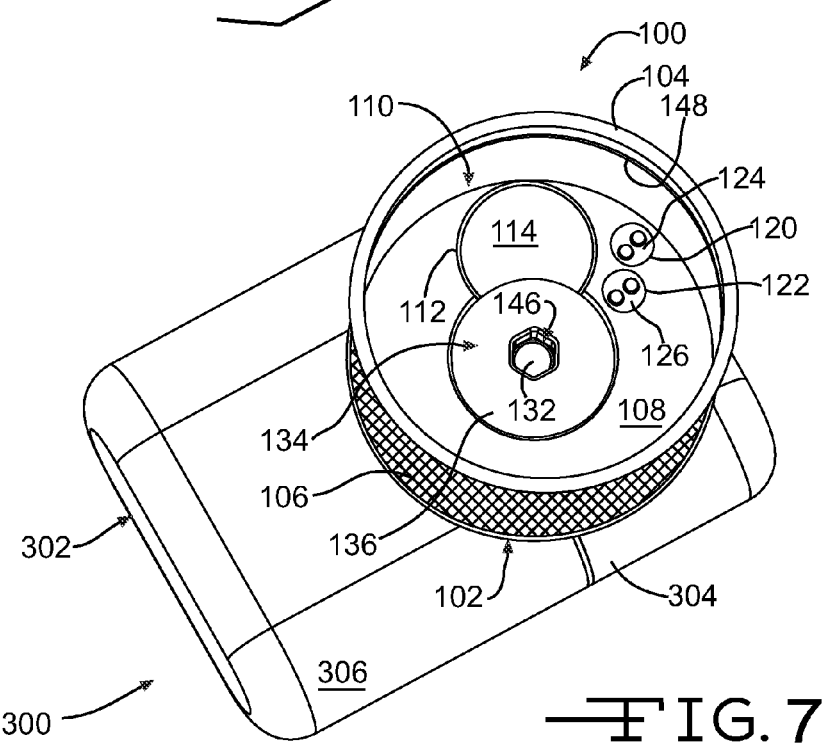
FIG. 7 is a perspective view of a portion of the medical device illustrated in FIGS. 2 and 3.
Figure 7A:
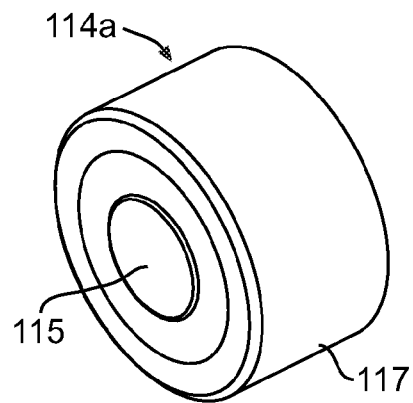
FIG. 7A is a perspective view of a rechargeable battery.
Figure 7B:
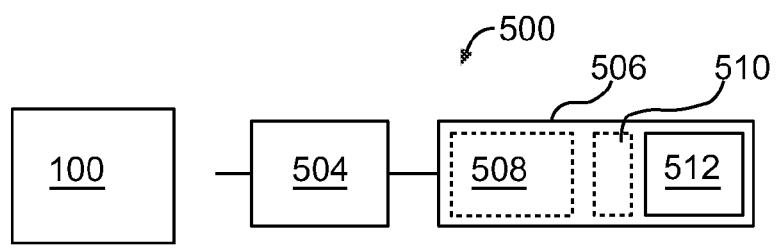
FIG. 7B is a block diagram in accordance with one embodiment of a present invention.
Figure 7C:
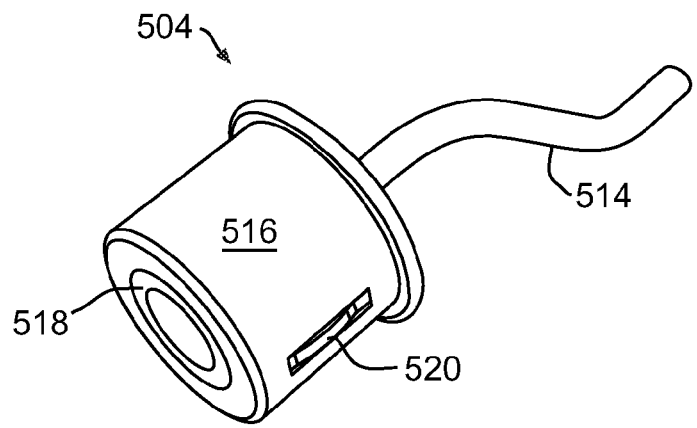
FIG. 7C is a perspective view of a portion of a charger in accordance with one embodiment of a present invention.
Figure 8:
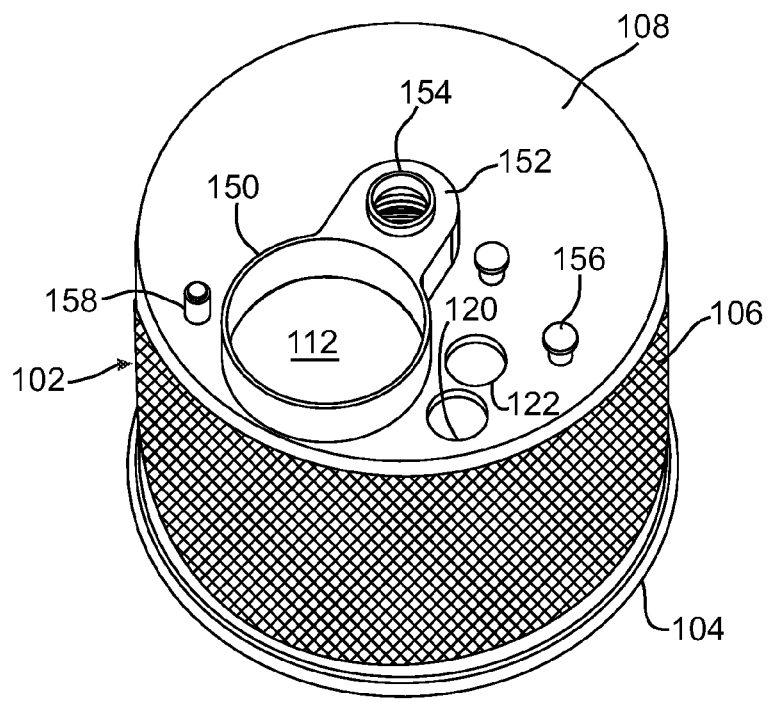
FIG. 8 is a perspective view of a portion of a percutaneous port in accordance with one embodiment of a present invention.

It should also be noted that a rechargeable battery may be used in place of the replaceable batteries 114. Referring first to FIG. 7A, the exemplary rechargeable battery 114a, which includes positive and negative contacts 115 and 117, may be inserted into the battery case 116 (FIG. 6) in place of batteries 114. A recharger that is configured to recharge the battery 114a by way of the percutaneous port 100 may also be provided. One example of such a charger, which is generally represented by reference numeral 500, is illustrated in FIGS. 7B and 7C. The exemplary charger 500 includes a power supply 502 and plug 504. The power supply 502 may include a housing 506, a power source 508 (e.g. one or more batteries), suitable control circuitry 510, and a user interface 512. The housing 506 may be configured to be worn (e.g. with a belt clip). The plug 504, which may be connected to the power supply 502 by a cable 514 and inserted into the percutaneous port 100, includes a housing 516 with an overall size and shape similar to that of the cartridge 200. The housing 516 carries positive and negative contacts 518 and 520. The positive contact 518 has an annular shape is sized and located such that it will engage one or both of the positive contacts 170a and 172a (discussed below), but not the negative contacts 172a and 172b, of sensors 124 and 126 when the plug 514 is inserted into the percutaneous port 100, regardless of rotational orientation, while the negative contact 520 will engage the inner surface of the tubular wall 102.

The charger 500 may be used to recharge the battery 114a when, for example, the cartridge 200 is being replaced. The user will simply remove the cartridge 200 from the percutaneous port 100, insert the plug 504, and actuate the power supply 502. After the battery 114a is fully charged, the plug 504 may be removed and a new cartridge 200 may be inserted into the percutaneous port 100.

Figure 20:
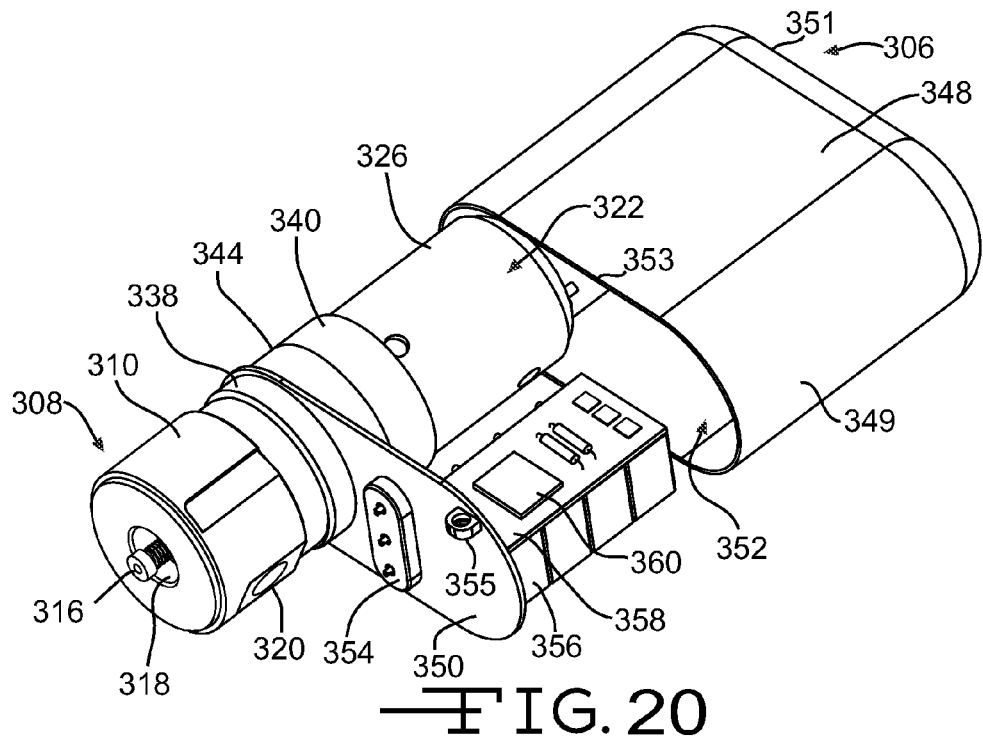
FIG. 20 is an exploded perspective view of a portion of the medical device illustrated in FIGS. 2 and 3.
Figure 21:
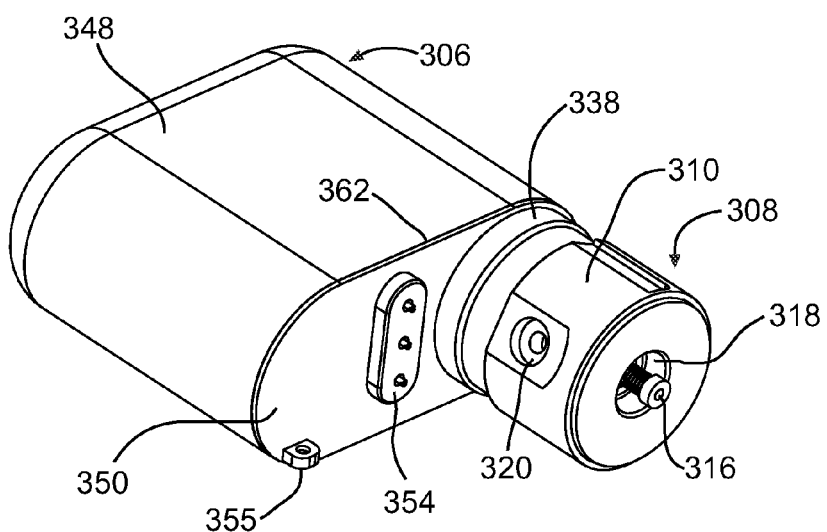
FIG. 21 is a perspective view of a portion of the medical device illustrated in FIGS. 2 and 3.

The exemplary fluid transfer device 308 may also include a portion of the housing electronics section 306. Referring to FIGS. 20 and 21, the housing electronics section 306 includes a hollow main portion 348 and a cover 350 that together enclose an interior 352. The hollow main portion 348 includes one or more side walls 349, a closed end wall 351 and an opening 353 that is closed by the cover 350. The cover 350, which includes a feed-through 354 (e.g. a three pin feed-through) and a pin receiver 355, is carried by the weld ring 338 in the illustrated embodiment. The cover 350 may, alternatively, be carried by other portions of the underlying fluid transfer device depending upon the type of fluid transfer device being employed and the manner in which the fluid transfer device is constructed. The cover 350 may be an integral part of the weld ring 338, or the cover and weld ring may be separately fabricated and welded or otherwise secured to one another.

Various electronic components, such as the capacitors 356 (e.g. potted or unpotted tantalum capacitors) that drive the electromagnet 322 and a circuit board 358 with a controller 360, such as a microprocessor, microcontroller or other control circuitry, are carried within the interior 352. Other electronic components may include, depending upon the particular implementation, an antenna to enable telemetry. The cover 350 may be welded to main portion 348 (note weld 362) and, to that end, the cover may be provided with a stepped perimeter (not shown) that aligns the cover with the main portion. The main portion 348 and the cover 350, together with the weld rings 338 and 340, the barrier 342 and the weld 344, hermetically seal the interior 352 of the electronics section 306 from the patient and the remainder of the medical device 20.

The main portion 348 or cover 350 may include a very small hole (not shown) that remains open during the assembly process. After the cover 350 is welded to the main portion 348, the interior 352 is vacuum baked and filled with an inert gas or combination of gasses, such as argon and helium. The hole may then be welded shut to trap the inert gas (or gases) within the interior 352 to protect the electronics and also to enable detection of helium to verify any leakage.

Figures 22, 23:
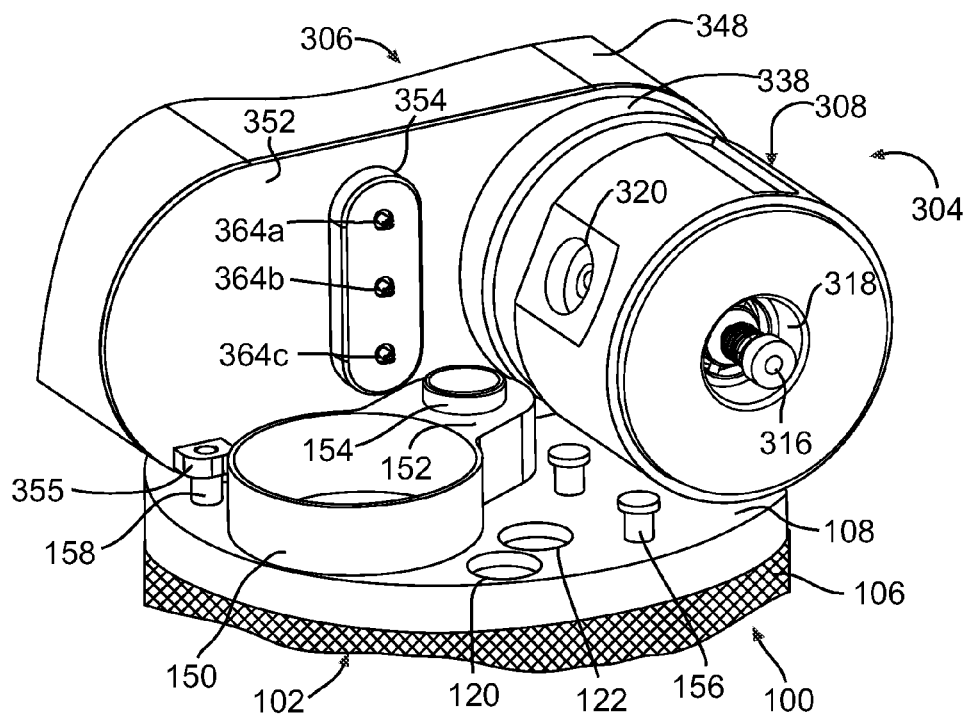
FIG. 22 is a perspective view of a portion of the medical device illustrated in FIGS. 2 and 3.
FIG. 23 is a perspective view of a portion of the medical device illustrated in FIGS. 2 and 3.

Referring to FIGS. 22 and 23, the components sealed within the interior 352 are electrically connected to the positive battery contact 118 and to the sensors 124 and 126 by way of the pins 364a-c on the three-pin feed-through 354. More specifically, wire 184a connects the contacts 170a and 172a of sensors 124 and 126 to the positive contact 118 which is, in turn, connected to pin 364a by wire 184b. Wire 184c connects contact 170b of sensor 124 to pin 364b, and wire 184d connects contact 172b of sensor 126 to pin 364c. Additionally, and as alluded to above, the flat retainer disk 136 on the percutaneous port 100 functions as the negative battery contact. The flat retainer disk 136 is electrically connected to the electronics section cover 350 by way of the percutaneous port end wall 108, the pin 158 and the pin receiver 355. The feed-through pins 364a, 364b and 364c are attached by welding the plate substrata to the cover 350, sealing the electronics section. The ground contact(s) on the circuit board 358 may be connected to the inner surface hollow main portion 348 or cover 350 of housing electronics section 306 by, for example, a wire (not shown) and a laser weld, resistance weld or conductive epoxy. Such an arrangement allows the battery voltage to be used for sensing purposes in the manner described in Section VI below.

There are a variety of advantages associated with hermetically sealing the electronics section 306 of the housing 302. For example, it is far easier to hermetically seal only that portion of the medical device that includes electronics than it is to hermetically seal the entire device. In particular, the present hermetic seal is formed by various medical device housing structures, the fluid transfer device and two simple welds. Another advantage is associated with the fact that smaller, unpotted capacitors may be employed because the capacitors are protected, thereby reducing the overall size of the medical device.

Figure 24:
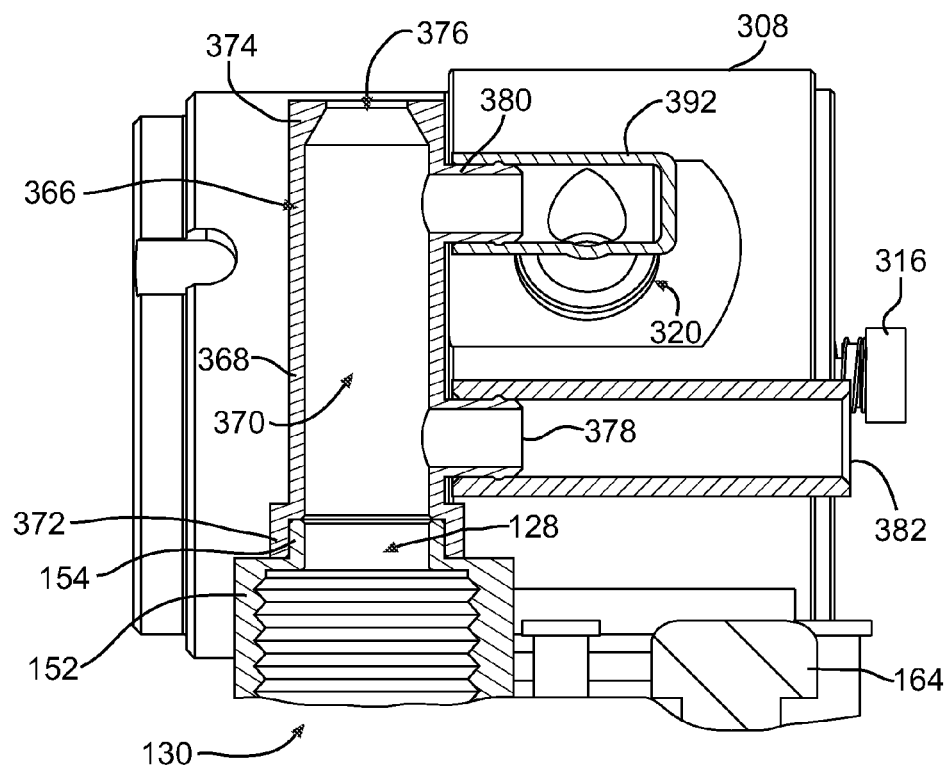
FIG. 24 is a section view of a portion of the medical device illustrated in FIGS. 2 and 3.
Figures 25, 26:
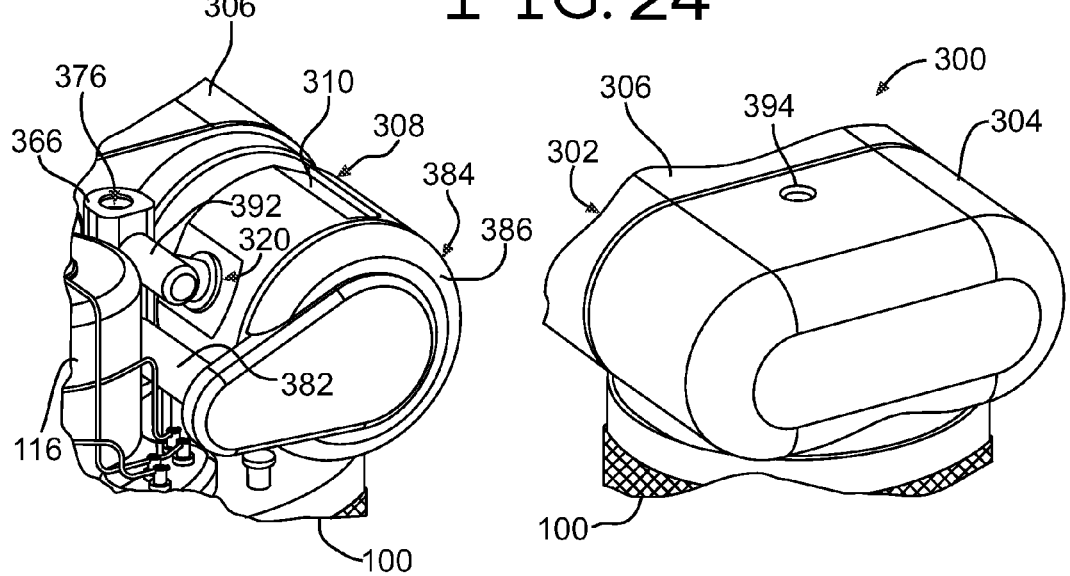
FIG. 25 is a perspective view of a portion of the medical device illustrated in FIGS. 2 and 3.
FIG. 26 is a perspective view of a portion of the medical device illustrated in FIGS. 2 and 3.
Figure 27:
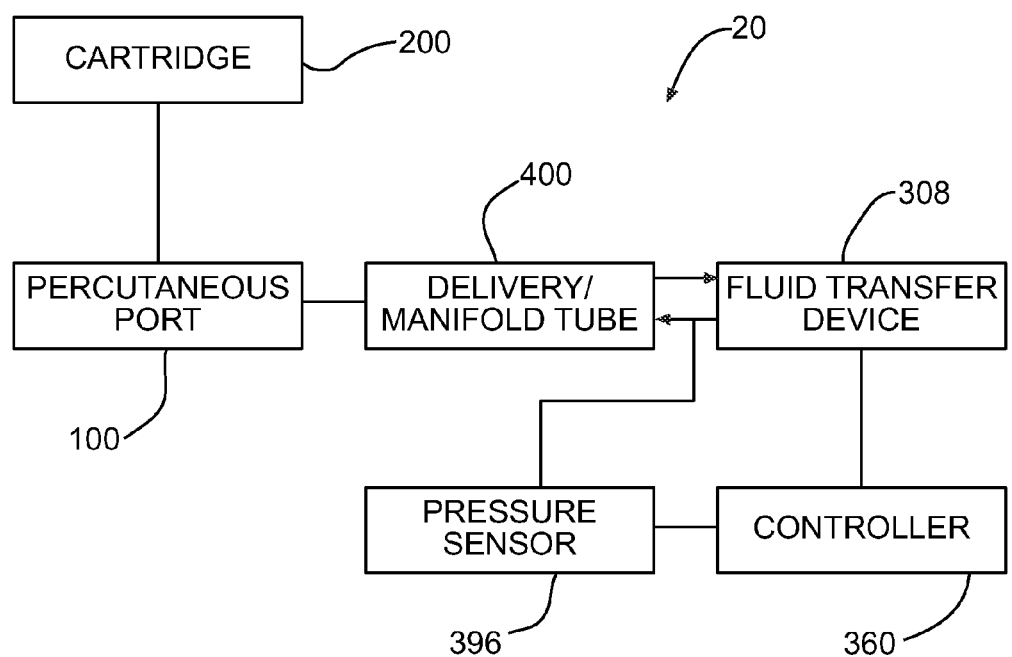
FIG. 27 is a block diagram in accordance with one embodiment of a present invention.

Turning to the fluid transfer apparatus within the fluid transfer section 304 of the housing 302, and referring first to FIGS. 23 and 24, a delivery/manifold tube receiver 366 is mounted onto the percutaneous port base member 152 in the exemplary embodiment. The exemplary delivery/manifold tube receiver 366 includes a tubular body 368 with an internal lumen 370 that is aligned with the percutaneous port apertures 128 and 130 (FIG. 6). A base 372, which is configured to fit over the ring 154 (FIG. 22), is located on one end of the tubular body 368. An internal abutment 374 and an aperture 376 are located at the other end of the tubular body 368. The internal abutment 374 and aperture 376 cooperate with various portions of the delivery/manifold tube 400 in the manner discussed in Section V below.

The exemplary delivery/manifold tube receiver 366 also includes a pair of longitudinally spaced outlet and inlet ports 378 and 380. As illustrated in FIGS. 23-28, the outlet port 378 may be connected to the inlet 318 of the fluid transfer device 308 by way of a connector tube 382 and a header 384. The header 384 includes a base 386 that is mounted onto the fluid transfer device housing 310, a connector 388 for the connector tube 382, and an internal lumen 390 that allows fluid to flow from the connector tube to the fluid transfer device inlet 318 (FIG. 28). The inlet port 380 is connected to the fluid transfer device outlet 320 by a connector tube 392. The outlet and inlet ports 378 and 380 are separated from one another by the delivery/manifold tube 400, which discussed in Section V below.

Suitable materials for the delivery/manifold tube receiver 366, the connector tubes 382 and 392, and the header 384 include, but are not limited to, polyethylene, polycarbonate and PEEK. Adhesive may be used to secure the delivery/manifold tube receiver 366 to the base member 152, the connector tubes 382 and 392 to the delivery/manifold tube receiver, the header 384 and fluid transfer device outlet 320, and the header to the fluid transfer device housing 310.

The fluid transfer section 304 of the housing 302 may be in the form of a hollow structure that is similar to that associated with the electronics section 306 and configured to mate with the percutaneous port 100. In the illustrated embodiment, however, the fluid transfer section 304 of the housing 302 is an electrically insulating material (e.g. epoxy) that is molded over and around the structures illustrated in FIGS. 22-25 to form the fluid transfer section illustrated in FIGS. 2, 3 and 26. The insulating material also secures itself to the anchors 156. An insert may be positioned over the delivery/manifold tube receiver 366 during the molding process in order to produce the lumen 394 that extends from the aperture 376 to the exterior of the housing 302. The lumen 394 facilitates passage of the delivery portion 402 of the delivery/manifold tube 400, which is discussed in Section V below.

The size and shape of the partially implantable medical device 20, especially the size and shape of the combined percutaneous port 100 and implantable operative portion 300, are advantageous for a variety of reasons. In the exemplary context of insulin delivery and the exemplary 1.8 cc cartridge described in Section III above, one implementation of the partially implantable medical device 20 may be sized as follows. The percutaneous port 100 has an inner diameter of about 15 mm and is about 12 mm in height. The exemplary implantable operative portion 300 is about 25 mm long, about 18 mm wide, and about 8 mm in height. With respect to shape, as can be seen in FIGS. 2, 3 and 5, the overall shape of the combined percutaneous port 100 and implantable operative portion 300 is that of a right angle (or an "L"). As such, the partially implantable medical device 20 may be inserted into the patient with a relatively small incision. Additionally, once the cartridge 200 is in place and is the only visible portion of the partially implantable medical device 20, the device will not be particularly noticeable.

It should also be noted here that the implantable operative portion 300 may, in some implementations, be provided with apparatus which perform the function of detecting blockages of the delivery portion 402 of the delivery/manifold tube 400 and alerting the patient to the presence of the blockage. As illustrated for example in FIG. 27, a pressure sensor 396 may be used to sense the pressure between the fluid transfer device 308 and the delivery portion 402 of the delivery/manifold tube 400. The pressure sensor 396 may also be connected to the controller 360. The controller 360 may use the sensed pressure to detect blockages and to determine whether or not the fluid transfer device 308 is functioning properly. The controller 360 may perform a variety of different functions in response to determination that there is a blockage or an improperly functioning fluid transfer device 308. For example, the controller 360 may actuate an audible and/or vibratory alarm (not shown) that is located within the housing 302.

V. Exemplary Delivery/Manifold Tube

One example of a removable delivery/manifold tube is generally represented by reference numeral 400 in FIGS. 28 and 29. The exemplary delivery/manifold tube 400 includes a delivery portion 402, which provides a flow path from the implantable operative portion 300 to the target tissue region, and a manifold portion 404, which directs fluid from the cartridge 200 to the fluid transfer device 308 as well as from the fluid transfer device to the delivery portion 402.

In the illustrated embodiment, the exemplary delivery portion 402 consists of a tube 406, with a fluid lumen 408, that extends outwardly from the implantable operative portion 300 in the manner illustrated in FIGS. 2 and 3 to the target region. In the exemplary context of insulin delivery, the implantable operative portion 300 may be located subcutaneously, but outside the peritoneal cavity, and the delivery portion 402 may extend through the peritoneum and into the peritoneal cavity, as illustrated in FIG. 5.

The exemplary manifold portion 404 illustrated in FIGS. 28 and 29 is configured to fit within delivery/manifold tube receiver 366 such that a seal is created therebetween. To that end, the manifold portion 404 includes a cylindrical main body 410, which has an outer diameter that is substantially equal to the diameter of the delivery/manifold tube receiver inner lumen 370, and a plurality of o-ring gaskets 412. It should be noted, however, that the frictional engagement between the delivery/manifold tube receiver 366 and the manifold portion 404 is not so great that it prevents the delivery/manifold tube 400 from being removed and replaced by way of the percutaneous port 100. The o-ring gaskets 412 are carried within indentations 414 that are formed in the main body 410. The main body 410 also includes a tapered portion 416 that abuts the internal abutment 374 when the manifold portion 404 is properly positioned within the delivery/manifold tube receiver 366. An o-ring gasket (not shown) may also be provided on the tapered portion 416. A pair of longitudinally spaced fluid lumens 418 and 420 are located within the main body 410, while a pair of longitudinally spaced annular indentations 422 and 424 are located on the exterior of the main body.

The fluid lumens 418 and 420 in the illustrated embodiment are separated from one another by a solid, lumen-free portion of the cylindrical main body such that fluid within lumen 418 is prevented from flowing directly into lumen 420. The fluid lumen 418 is also respectively aligned with, and in direct fluid communication with, the hollow region 178 of the septum 132 and the fluid lumen 408 is in direct alignment with the delivery portion 402. The indentations 422 and 424 and the surface of the inner lumen 370 together define a pair of longitudinally spaced annular fluid channels 426 and 428. The fluid channels 426 and 428 are separated by the portion of the cylindrical main body 410 that carries the o-ring gaskets 412 such that fluid within channel 426 is prevented from flowing directly into channel 428, and are respectively connected to the fluid lumens 418 and 420 by apertures 430 and 432. The apertures 430 and 432 extend through the cylindrical wall that defines the manifold portion 404.

The percutaneous port 100, the cartridge 200, the delivery/manifold tube receiver 366 and the delivery/manifold tube 400 are respectively configured such that, when the cartridge is fully inserted in the percutaneous port (FIG. 28), the cartridge needle 204 will extend through the septum 132. The needle apertures 244 will be located within the septum hollow region 178 or the delivery/manifold tube lumen 418. So positioned, fluid from the cartridge fluid storage volume 236 will flow through the needle 204 to the delivery/manifold tube lumen 418. From there, fluid will flow to the fluid transfer device inlet 318 by way of the apertures 430, the annular fluid channel 426, the outlet port 378, the connector tube 382 and the header 384. Fluid from the fluid transfer device outlet 320 will flow to the target body region by way of the connector tube 382, the inlet port 380, the annular fluid channel 428, the apertures 432, the lumen 420 and the lumen 408.

There are a variety of advantages associated with the present delivery/manifold tube 400 and the manner in which it is associated with the percutaneous port 100, the replaceable cartridge 200, and the implantable operative portion 300. By way of example, but not limitation, the delivery/manifold tube 400 may be removed from the implantable operative portion 300 (and the patient) by way of the percutaneous port 100, as necessary or desired, and replaced by way of the percutaneous port. Such removal and replacement may, for example, occur in response to the formation of a blockage at the outlet end of the lumen 408 or may simply be associated with periodic maintenance. In either case, the removal and replacement may be accomplished without a surgical procedure. The delivery/manifold tube 400 also simplifies the assembly process by obviating the need for separate structures that would have provided the same functionality as well as the connectors and seals associated therewith.

With respect to materials, the delivery portion 402 may be formed from relatively soft materials such as silicone rubber, TEFLON PTFE, polyethylene, polyurethane and Vectra® liquid crystal polymer, while the manifold portion 404 may be formed from a hard plastic such as PEEK or TEFLON PTFE or a metal such as titanium. The delivery portion 402 and manifold portion 404 may, in other implementations, be formed from the same materials.

It should also be noted there that there may be some instances where it is desirable to provide a protective passageway for the delivery portion 402 of the delivery/manifold tube 400 in order to insure effective placement and removal. One example of an apparatus that provides such a passageway is described in Section VII below.

VI. Exemplary Control Methodologies

Partially implantable medical devices in accordance with the present inventions may be programmed and/or controlled in any suitable manner. For example, some implementations of the present partially implantable medical devices may include an antenna and receive instructions and/or programming information by way of a telemetric programmer. Some implementations of the present partially implantable medical devices may include a data connector (e.g. a micro-USB connector within the percutaneous port 100 and under the flat retainer disk 136 of the retainer 134) that can receive instructions and/or programming information by way of wired connection to a programmer. Programmers and the controller 360 may also be configured such that instructions and programming information may be delivered by way of the control sensor contacts 170a/170b and 172a/172b.

Alternatively, or in addition, the percutaneous port and cartridge may be configured to function as a user interface that allows the physician and/or patient to control various aspects of the operation of the associated partially implantable medical device and/or to input programming commands while implanted in the manner illustrated in FIGS. 4 and 5. In the illustrated implementation, and as alluded to above, the percutaneous port 100 includes a cartridge sensor. More specifically, in the exemplary implementation, the cartridge sensor consists of a pair of circumferentially spaced control sensors 124 and 126, and the cartridge 200 includes a plurality of spaced sensible members 250. The contacts 170a and 170b on sensor 124 are respectively connected to positive and negative battery terminals, and the contacts 172a and 172b on sensor 126 are respectively connected to positive and negative battery terminals. The exemplary spaced sensible members 250 are electrically conductive pads. Current will flow from contact 170a to contact 170b when the contacts are both aligned with one of the electrically conductive pads 250, and the switch defined by the contacts and pad is closed. Similarly, current will flow from contact 172a to contact 172b when the contacts are both aligned with one of the electrically conductive pads 250, and the switch defined by the contacts and pad is closed. A non-zero voltage across contacts 170a/170b and/or contacts 172a/172b (and, accordingly, pins 364a/364b and/or pins 364a/364c) represents the presence of a sensible member 250 that is aligned with control sensor 124 and/or control sensor 126. Put another way, in the illustrated implementation, the presence of a sensible member 250 at one of the control sensors 124 and 126 is sensed when the switch is closed.

Such sensing may be used by the controller 360 to determine the direction and magnitude of the rotational movement of the cartridge 200 relative to the percutaneous port 100, as is discussed below with reference to FIGS. 30-35. The number of times there is (and is not) a voltage across contacts 170a/170b and contacts 172a/172b (and, accordingly, pins 364a/364b and pins 364a/364c), and the order in which the on-off changes in voltage occur, is indicative of the magnitude and direction of the rotational movement of the cartridge 200 relative to the percutaneous port 100. The patient or physician may simply rotate the cartridge 200 in a predetermined manner to input commands and/or otherwise interface with the exemplary medical device 20, as is discussed below with reference to FIG. 36.

The exemplary sensible members 250 from the cartridge 200 are superimposed over the end wall 108 and control sensors 124 and 126 of the percutaneous port 100 in FIGS. 30-35 to illustrate the changes in the relative rotational orientations of the sensible members and control sensors that occur when a cartridge is located within the percutaneous port of an implanted medical device and rotated relative thereto.

Figure 30:
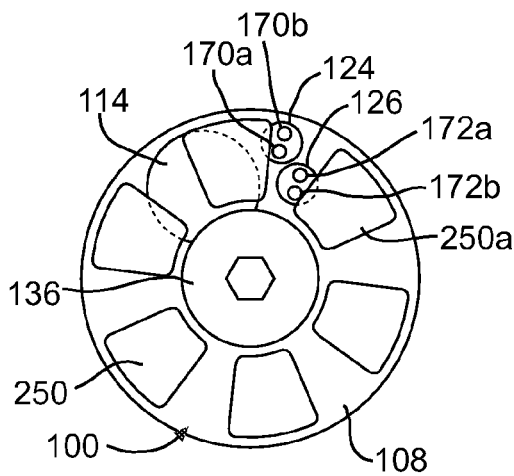
FIGS. 30-35 are plan views showing a plurality of sensible members moving relative to a pair of sensors.

FIG. 30 represents one exemplary initial orientation of the sensible members 250 and cartridge 200 (not shown) relative to the percutaneous port 100. No sensible member 250 is aligned with the contacts on either of the control sensors 124 and 126 in the illustrated rotational orientation and, accordingly, no sensible member is sensed at either of the control sensors (a "124-no/126-no" state). Of course, and as will be clear from the discussion below, the initial rotational orientation of the sensible members 250 (and cartridge 200) need not be that shown in FIG. 30.

Figure 31:
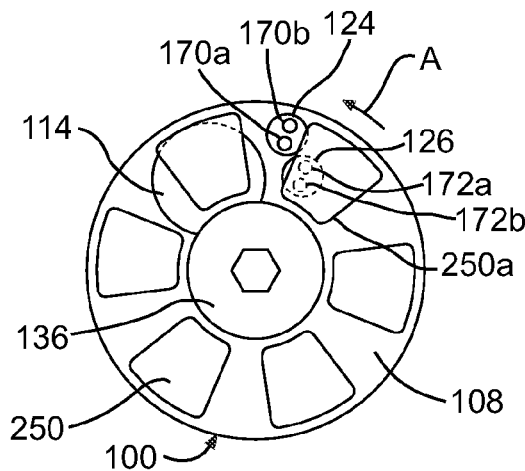

In FIG. 31, the sensible members 250 (and cartridge 200) have been rotated relative to the percutaneous port 100 in the direction of arrow A such that the sensible member 250a is aligned with the contacts 172a/172b of control sensor 126 and no sensible member is aligned with the contacts 170a/170b of control sensor 124. A sensible member will, accordingly, not be sensed at control sensor 124 and will be sensed at control sensor 126 (a "124-no/126-yes" state). The transition from the 124-no/126-no state to the 124-no/126-yes state indicates that the sensible members 250 (and cartridge 200) are moving in the counter-clockwise direction.

Figure 32:
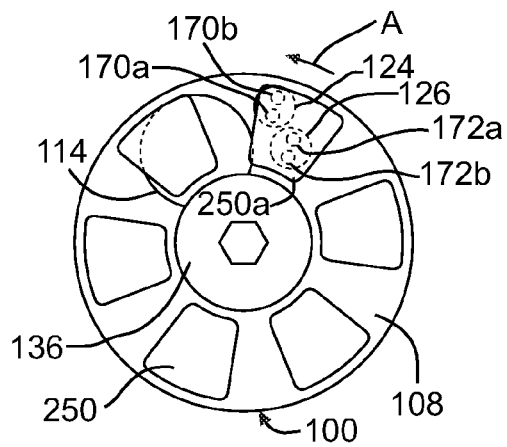

Turning to FIG. 32, the sensible members 250 (and cartridge 200) have been further rotated relative to the percutaneous port 100 in the direction of arrow A such that the sensible member 250a remains aligned with the contacts 172a/172b of control sensor 126 and the sensible member 250a is now also aligned without the contacts 170a/170b of control sensor 124. A sensible member will, accordingly, be sensed at both control sensor 124 and control sensor 126 (a "124-yes/126-yes" state). The transition from the 124-no/126-yes state to the 124-yes/126-yes state, without reversion to the prior 124-no/126-no state, indicates that the cartridge 200 is continuing to move in the counter-clockwise direction without any appreciable movement in the clockwise direction.

Figure 33:
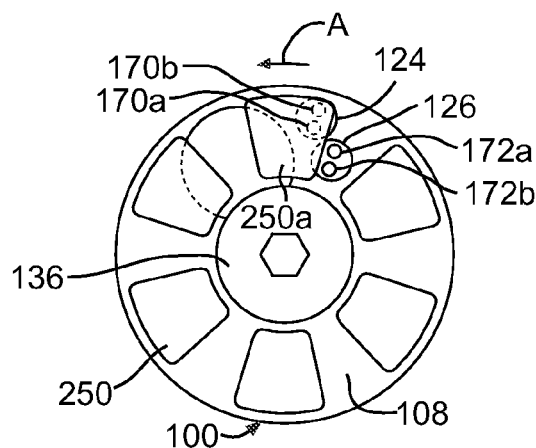

The sensible members 250 (and cartridge 200) in FIG. 33 have been further rotated relative to the percutaneous port 100 in the direction of arrow A such that the sensible member

250*a* is no longer aligned with the contacts 172*a*/172*b* of control sensor 126 and the sensible member 250*a* remains aligned with the contacts 170*a*/170*b* of control sensor 124. A sensible member 250 will, accordingly, be sensed at control sensor 124 and not sensed at control sensor 126 (a "124-yes/126-no" state). The transition from the 124-yes/126-yes state to the 124-yes/126-no state, without reversion to the prior 124-no/126-yes state, indicates that the cartridge is continuing to move in a counter-clockwise direction without any appreciable movement in the clockwise direction.

A subsequent transition from the 124-yes/126-no state to the 124-no/126-no state (i.e. the initial state), without reversion to the prior state, will indicate that the movement has continued in the direction of arrow A and, in the context of the illustrated implementation, that there has been a single sensor cycle and that the cartridge has rotated a total of about 60 degrees from the initial location (FIG. 30). Continued rotation in the direction of arrow A to the location illustrated in FIG. 34, i.e. 180 degrees from the initial location (FIG. 30), will result in two more sensor cycles. Again, each sensor cycle is a transition from 124-no/126-no state to another 124-no/126-no state in the manner described above, and each cycle represents a rotation of 60 degrees.

It should be noted here that the 124-no/126-no state need not be the initial state when monitoring rotational movement of the cartridge 200 relative to the percutaneous port 100. The initial state is merely the state present when rotational movement begins after a predetermined period without rotational movement (e.g. at least 5-10 seconds). If, for example, a sensible member 250 is aligned with the contacts on both of the control sensors 124 and 126, then the initial state will be the 124-yes/126-yes state, and a cycle will be a transition from a 124-yes/126-yes state to another 124-yes/126-yes state.

Figure 34:
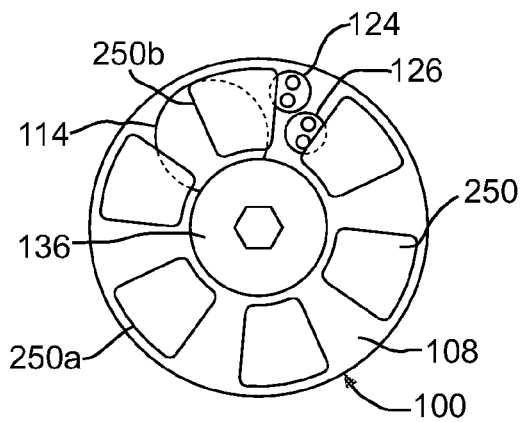
Figure 35:
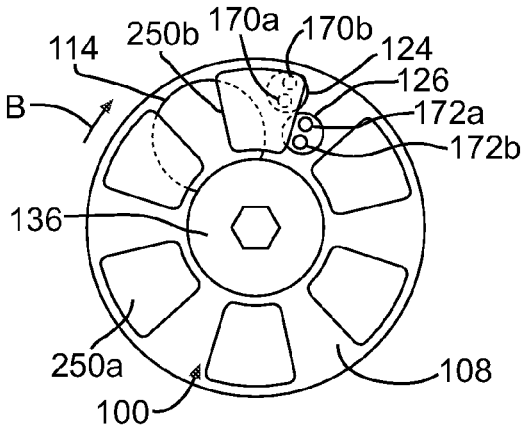

Rotational movement in the opposite direction is sensed in essentially the same way, although the yes/no transitions will occur in a different order. For example, FIGS. 34 and 35 show the rotation of the sensible members 250 (and cartridge 200) relative to the percutaneous port 100 in the direction of arrow B. The sensible member 250*b* will be sensed at control sensor 124 and not sensed at control sensor 126 in FIG. 35. The transition from the 124-no/126-no state (FIG. 34) to the 124-yes/126-no state (FIG. 35) indicates that the cartridge is moving in a clockwise direction.

Regardless of the type of sensors and sensible members that are employed, and the manner in which the sensors and sensible members are used to identify rotational movement of the cartridge 200 relative to the percutaneous port 100, the ability to identify and track such rotational movement facilitates the use of the percutaneous port and the cartridge as a user interface. By way of example, but not limitation, a variety of user-initiated implantable medical device operations may be pre-programmed into the partially implantable medical device and such operations may be actuated by the port/cartridge user interface. Each user-initiated operation may be assigned a unique defined cartridge rotational movement or a unique defined combination of rotational movements (collectively "defined cartridge rotational movement"). A time limit will be applied in at least some embodiments. Here, a defined cartridge rotational movement will not be effective unless the combination completed within a predetermined time period (e.g. about 15 seconds from the initial detection of rotation).

Figure 36:
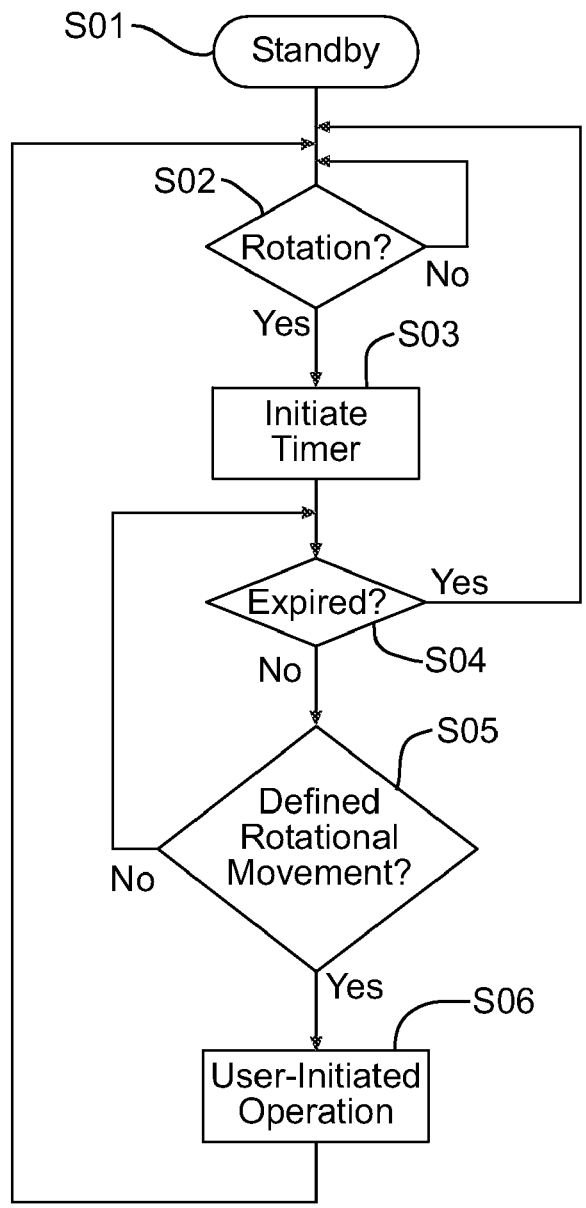
FIG. 36 is a flow chart in accordance with one embodiment of a present invention.

The general operation of the user interface and the associated aspects of the controller 360 is graphically illustrated in FIG. 36. More specifically, with respect to user-initiated operation, the controller 360 will remain in a standby state (step S01) until rotational movement of the cartridge is sensed (step S02). A timer is initiated in response to the sensing of cartridge rotation (step S03). If one of the defined cartridge rotational movements is received prior to the expiration of the predetermined period (steps S04 and S05), then the user-initiated operation associated with the defined cartridge rotational movement will be initiated (step S06). If, on the other hand, one the defined cartridge rotational movements is not received prior to the expiration of the predetermined period (steps S04 and S05), the controller 360 will return to the standby state with respect to the user interface aspects of its operation.

For example, an operation may be initiated in response to the following cartridge rotational movement: at least 360 degrees in one direction followed by rotation of at least 360 degrees in the opposite direction, with both rotations occurring within 15 seconds of the initiation of the first rotation. Another exemplary rotation combination is rotation of at least 180 degrees in a particular direction that is completed within 15 seconds of the initiation of the rotation. The controller 360 may also be configured to actuate an audible and/or vibratory alarm (not shown) that is located within the housing 302 in response to a successful input of a defined cartridge rotational movement and/or an unsuccessful input attempt. Different versions of the alarm (e.g. one beep vs. two beeps) should be used when the alarm is actuated in response to both successful and unsuccessful attempts.

With respect to the user-initiated operations themselves, one example involves a reduced delivery rate mode that may be pre-programmed into the partially implantable medical device 20. The reduced delivery rate mode may be configured to end after a predetermined period, so that the implantable operative portion 300 will automatically return to the programmed rate, or may be configured to continue until disabled. In the exemplary context of basal insulin delivery, the reduced delivery rate mode may be useful during exercise and may cause the implantable operative portion 300 to deliver insulin at a lower level such as 50% of the programmed basal rate for a predetermined period, such as 30 minutes.

Another exemplary user-initiated operation is bolus delivery. In the exemplary context of basal insulin delivery with the partially implantable medical device 20, the user may initiate a mealtime bolus if necessary. The delivery of pain medication is another area in which a patient controlled bolus may be desirable.

Still other exemplary user-initiated operations involve changing basal delivery rates. A plurality of rates may be pre-programmed into the partially implantable medical device 20. The user interface defined by the percutaneous port 100 and cartridge 200 may be used to increase or decrease the delivery rate in step fashion from one pre-programmed rate to another each time a predetermined combination has been entered. Alternatively, the partially implantable medical device may simply store a single basal rate and the user interface may be used to increase or decrease the delivery rate by predetermined amounts each time a predetermined combination has been entered.

There are a variety of advantages associated with a user interface that is defined by the percutaneous port 100 and cartridge 200. By way of example, by not limitation, the present user interface obviates the need for the patient to possess a telemetric remote control and, accordingly, obviates the expense and potential inconvenience (if lost or otherwise unavailable) associated a remote control. The present user interface may also eliminate the need for telemetric control by the physician, thereby eliminating the need for an antenna and associated telemetric circuitry in the partially implantable medical device.

VII. Exemplary Internal Port

Figure 37:
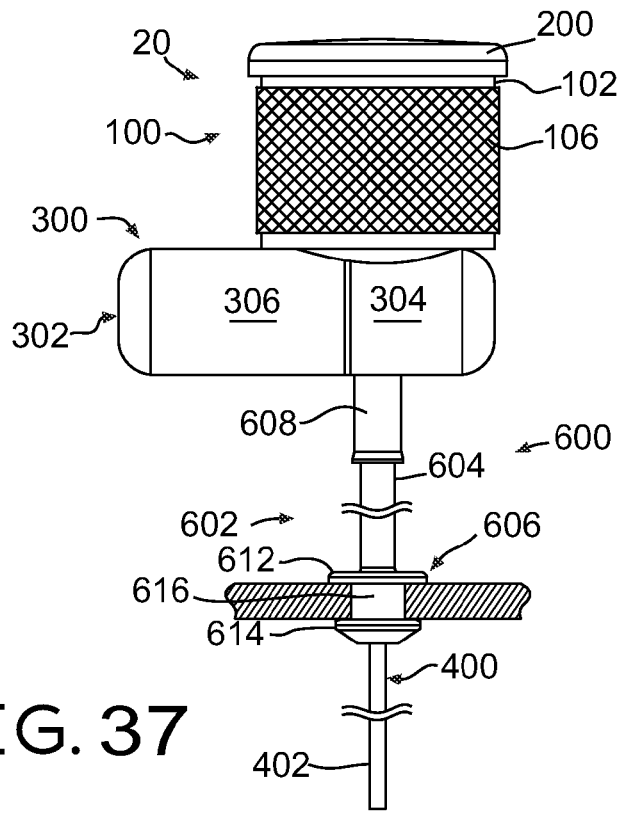
FIG. 37 is a side view of a medical device in accordance with one embodiment of a present invention.

As alluded to above, there may be some instances where it is desirable to provide a protective passageway for the delivery portion 402 of the delivery/manifold tube 400 in order to insure effective placement and removal. In the exemplary context of the intraperitoneal delivery, fat, muscle or the peritoneal wall can interfere with delivery and/or removal. One example of an apparatus that provides such a passageway is the internal port generally represented by reference numeral 600 in FIGS. 37 and 38. The exemplary internal port 600 includes a guide 602, with an elongate tube 604 and anchor 606, and a connector 608 that extends from the implantable operative portion housing 302 and over a portion of the guide.

The elongate tube 604 of the exemplary guide 602 defines an internal lumen 610 and may be cut to length depending on the patient's physique and the location within the body. The anchor 606 includes top and bottom flanges 612 and 614 with a gap 616 therebetween. The top flange 612 is generally flat, while the bottom flange 614 has a tapered surface. The tapered surface makes it easier to push the bottom flange 614 though a previously formed opening in the peritoneal wall PW (or other tissue structure) that is smaller than the bottom flange. Once through, the tissue structure will be held within the gap 616 between the flanges 612 and 614, thereby fixing the position of the elongate tube 602.

The guide 602 may also configured to reduce the likelihood of tissue growth within the internal lumen 610 to prevent interference with the movement of the delivery/manifold tube 400, and to encourage tissue ingrowth on the exterior of elongate tube 604 and anchor 606 to prevent movement of the guide. Suitable materials for the guide 602 include, but are not limited to, an expanded polytetrafluoroethylene (ePTFE) material known as GORE-TEX from W. L. Gore & Associates, which is smooth on one side and rough on the other, and TEFLON PTFE with a roughened exterior.

Figure 38:
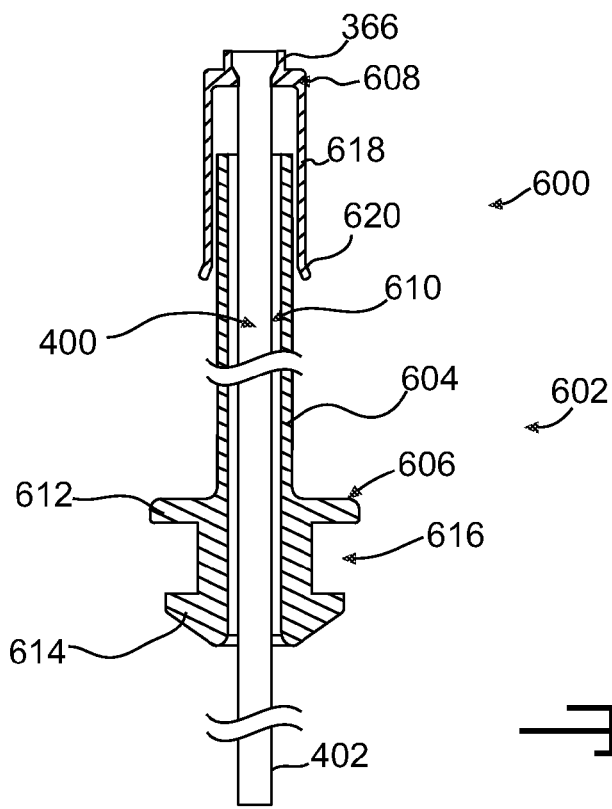
FIG. 38 is a partial section view of a portion of the medical device illustrated in FIG. 37.

The connector 608, which is used to align the housing lumen 394 (FIG. 26) with the guide 602, includes a relatively short tube 618 with an outwardly flared end 620. The flared end 620 facilitates positioning of the relatively short tube 618 over the elongate guide tube 604 during placement of the implantable operative portion 300 within the patient. The connector 608 may be secured to the exterior of the housing 300 during assembly. Alternatively, as shown in FIG. 38, the connector 608 may be integrally formed with the delivery/manifold tube receiver 366 described above with reference to FIGS. 23 and 26.

VIII. Other Exemplary Medical Devices With Percutaneous Ports

The present partially implantable medical devices are not limited to the exemplary implementations described above with reference to FIGS. 1-38. By way of example, but not limitation, a few additional implementations are described here.

Turning to FIGS. 39-42, the exemplary partially implantable medical device generally represented by reference numeral 20a is substantially similar to device 20 and similar elements are represented by similar reference numerals. For example, the partially implantable medical device 20a includes a percutaneous port 100a. Like port 100, the percutaneous port 100a has a tubular wall 102, a layer of porous material 106, sensors 124 and 126, a removable septum 132, and a releasable lock 134 that holds the septum 132 in place.

The percutaneous port 100a in the exemplary partially implantable medical device 20a illustrated in FIGS. 39-42 is not, however, mounted on the implantable operative portion 300a. The percutaneous port 100a is instead connected to the implantable operative portion 300a by a connector tube 400a. In the illustrated embodiment, the connector tube 400a is a dual lumen tube with a first lumen 401, which provides a fluidic connection from the cartridge to the implantable operative portion 300a, and a second lumen 403 for the wires (not shown) that connect the sensor contact pairs 170a/170b and 172a/172b (FIG. 9) to the feed-through 354 (FIG. 21) and the positive terminal of the battery. The percutaneous port 100a also includes a base 101, such as a epoxy molded base, in which the sensors 124 and 126 are carried. The first lumen 401 may be connected to the fluid transfer device inlet 318 (FIG. 22) by a slightly different header, and the fluid transfer device outlet 320 (FIG. 22) may be connected to an outlet 394a formed in the housing fluid transfer section 304a by a tube (not shown). Alternatively, the tube may extend though the outlet 394a and into the patient.

With respect to power, a battery or other energy storage device 114a is permanently carried within the electronics section 306a of housing 302a, and accordingly, the electronics section 306a will be larger than the electronics section 306, all other things being equal. The exemplary percutaneous port 100a does not, accordingly, include a battery case or battery aperture. In other implementations, a battery case (e.g. battery case 116 in FIG. 9) may be provided and carried within the base 101 and the positive and negative battery terminal would be connected to the electronics section 306a by way of wires that also extend through lumen 403. In still other implementations, the battery carried within the electronics section 306a will be relatively small and rechargeable by way of electrical contacts within the port 100a as described above with reference to FIGS. 7A-7C.

The exemplary implantable operative portion 300a may be positioned within the target region. In the exemplary context of insulin delivery, the implantable operative portion 300a may be positioned within the peritoneum. Alternatively, the implantable operative portion 300a may be positioned subcutaneously connected to the peritoneum by a delivery tube (not shown) that extends through peritoneal wall.

Another exemplary partially implantable medical device is generally represented by reference numeral 20b in FIG. 43. The exemplary partially implantable medical device generally represented by reference numeral 20b is substantially similar to device 20a and similar elements are represented by similar reference numerals. Here, however, the housing 302b is an elongate tubular structure. The inlet of fluid transfer device 308, which is located at one end of the housing 302b, is connected to the percutaneous port 100a by the connector tube 400a. The outlet of the of the fluid transfer device 308 may be connected to a delivery tube 402b (as shown) or to an outlet in the housing 302b. In the illustrated implementation, the battery 114b is located at the other end of the housing and an electronics compartment 306b including, for example, a controller and one or more capacitors, is located therebetween.

Partially implantable medical devices in accordance with at least some of the present inventions may also be powered by a power source carried by a replaceable cartridge. One example of such a partially implantable medical device is generally represented by reference numeral 20c in FIG. 44. The exemplary medical device 20c is substantially similar to medical device 20 and similar elements are represented by similar reference numerals. For example, partially implantable medical device 20c includes a percutaneous port 100c, a replaceable cartridge 200c, an implantable operative portion 300c with a housing 302 having a fluid transfer section 304 and an electronics section 306, and a replaceable delivery/manifold tube 400. Here, however, the percutaneous port 100c is configured to receive power for the operation of the medical device from a power source on the replaceable cartridge 200c.

Figure 44:
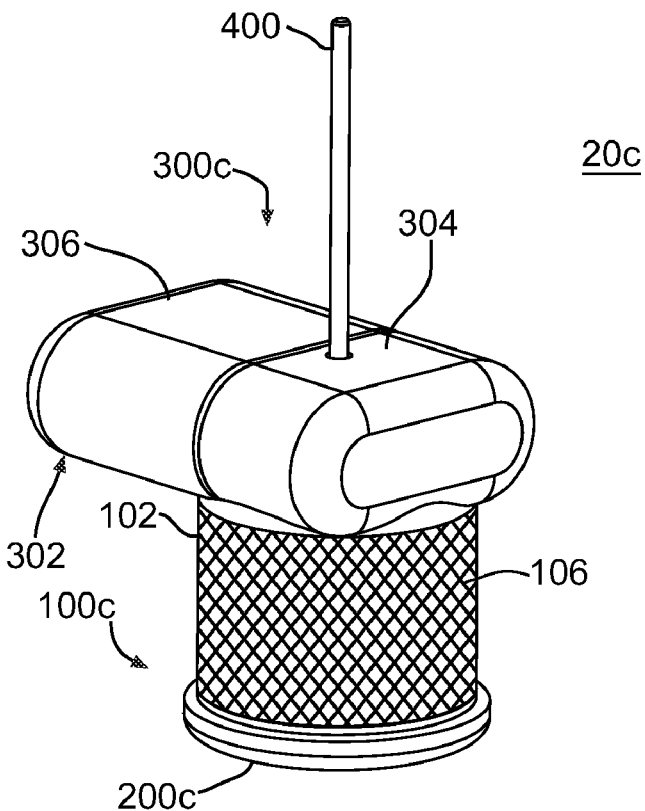
FIG. 44 is a perspective view of a medical device in accordance with one embodiment of a present invention.
Figure 45:
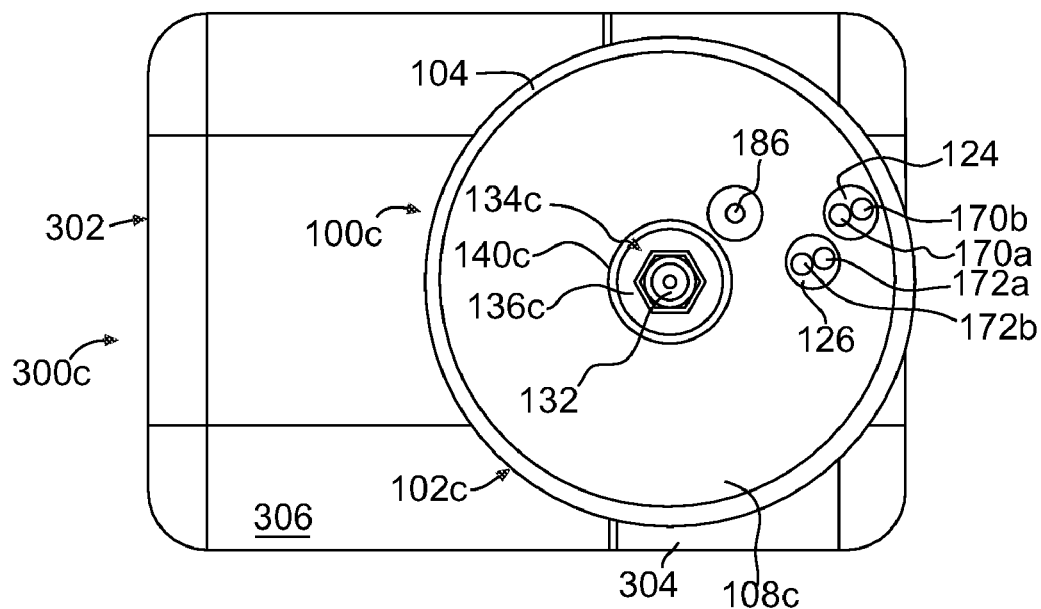
FIG. 45 is a plan view of a portion of the medical device illustrated in FIG. 44.

Referring to FIGS. 44 and 45, the exemplary percutaneous port 100c is similar to percutaneous port 100 in that port 100c includes a with a tubular wall 102, a rounded rim 104, a layer of porous material 106, an end wall 108c, control sensors 124 and 126, and a septum 132. Given that the replaceable cartridge 200c supplies the power for the medical device 20c, the percutaneous port 100c need not include a battery case or an aperture that allows batteries to be inserted into, and removed from, the battery case (note, for example, the aperture 112 and battery case 116 in FIG. 6). The exemplary percutaneous port 100c is instead provided with a power contact 186 that will be electrically connected to a power contact on the replaceable cartridge 300c when the cartridge is inserted into the port. The power contact 186, which is the positive power contact in the illustrated implementation, may be radially offset from the control sensors 124 and 126, and the power contact on the replaceable cartridge may be correspondingly located, to prevent interference with the functionality of the control sensors, as is described below with reference to FIGS. 49 and 50. The exemplary percutaneous port 100c may also be configured to prevent the power contact on the replaceable cartridge 300c from making an electrical connection with portions of the end wall 108c other than the power contact 186. In the illustrated implementation, the entire inner surface of the end wall 108c (i.e. the surface visible in FIG. 45) is electrically non-conductive. This may be accomplished by, for example, an oxidation treatment of the inner surface of the end wall 108c prior to assembly or by coating the inner surface with a durable non-conductive material, such as TEFLON PTFE, ceramic or glass, prior to assembly. In other implementations, only that portion of the end wall inner surface which could come into contact with the power contact on the replaceable cartridge 300c, e.g. the annular region radially inward of the control sensor 126, will be electrically non-conductive.

Figure 46:
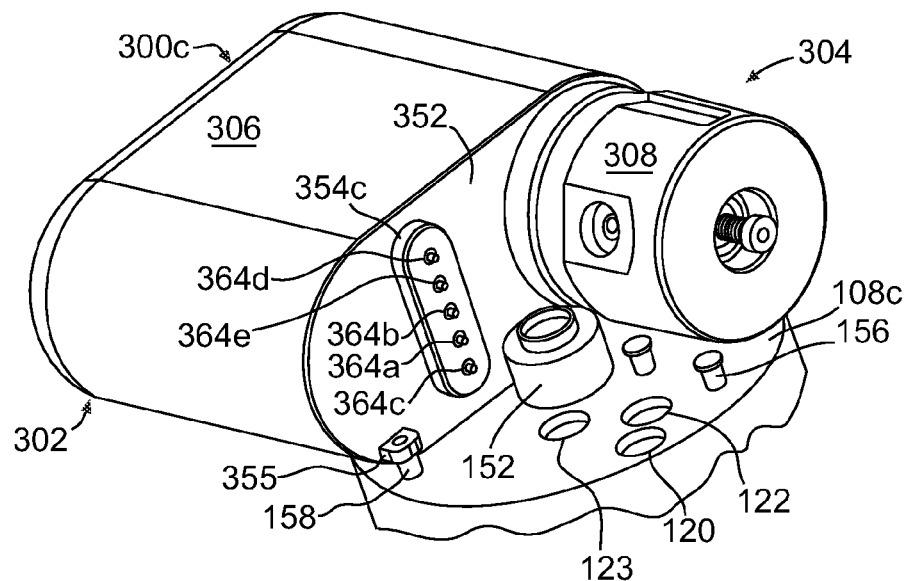
FIG. 46 is a perspective view of a portion of the medical device illustrated in FIG. 44.

The exemplary percutaneous port 100c is also provided with a retainer 134c that holds the septum 132 and the delivery/manifold tube 400 in place. The exemplary retainer 134c includes a flat retainer disk 136c, which is received in an indentation 140c, and a post (not shown) of the type described above with reference to FIG. 6. A power control aperture 123 (FIG. 46) is provided adjacent to the control sensor apertures 120 and 122.

Figure 47:
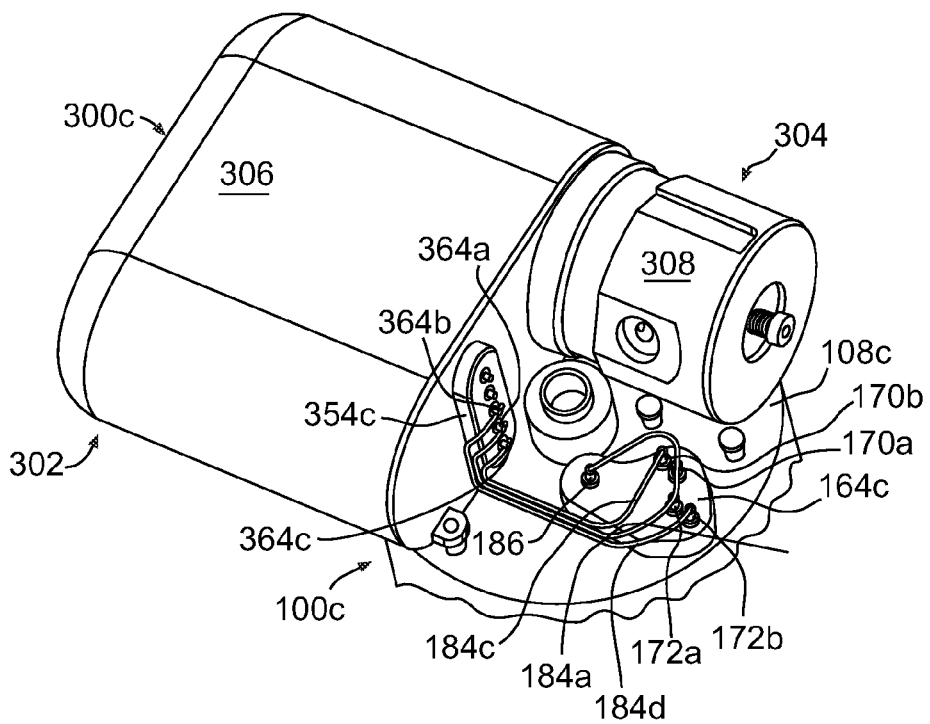
FIG. 47 is a perspective view of a portion of the medical device illustrated in FIG. 44.

Turning to FIG. 47, a base member 164c carries the control sensor contacts 170a/170b and 172a/172b, as well as the power contact 186, of the exemplary port 100c. Suitable electrically non-conductive materials for the base 164c include, but are not limited to, polyethylene, polycarbonate, and PEEK. The contacts 170a/170b, 172a/172b and 186 are connected to pins 364a-c on a multi-pin feed-through 354c as follows. Wire 184a connects the contacts 170a and 172a to the power contact 186 and to pin 364a. Wire 184c connects contact 170b to pin 364b, and wire 184d connects contact 172b to pin 364c. The percutaneous port 100c functions as the negative power contact, as is described below with reference to FIG. 50.

Figure 48:
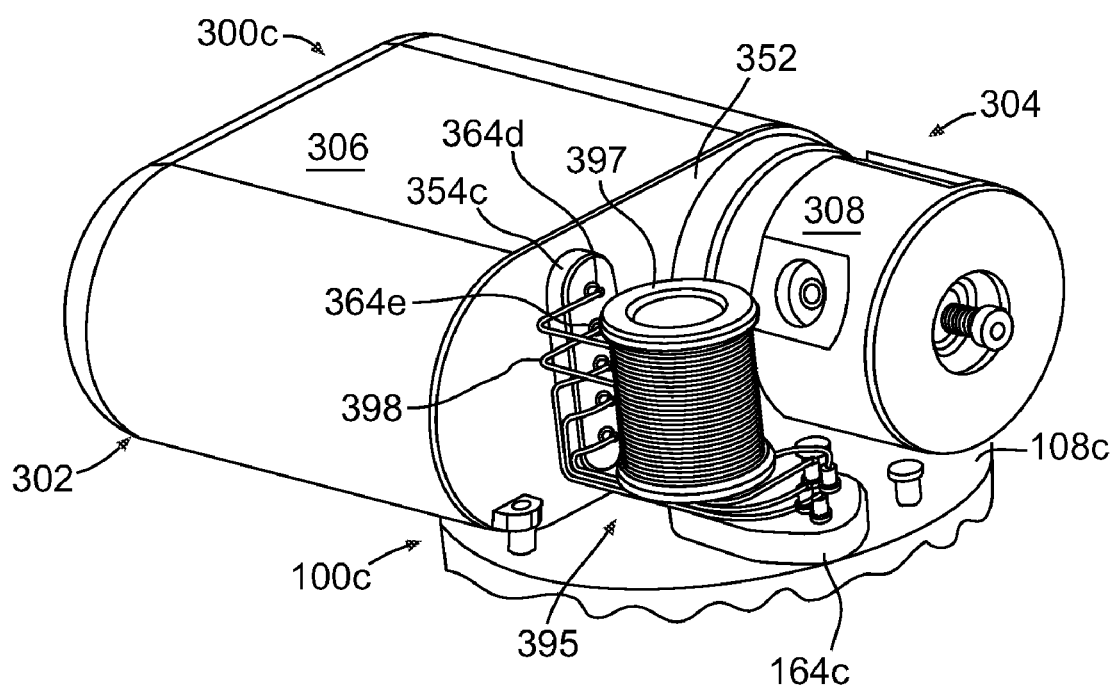
FIG. 48 is a perspective view of a portion of the medical device illustrated in FIG. 44.

The volume that would have otherwise been occupied by the battery case 116 (FIG. 6) may be accounted for in a variety of ways. The space may be occupied by the electrically insulating material that is molded around the structures within the fluid transfer section 304 in some implementations. The space may, in other implementations, be occupied by other aspects of the medical device so as to reduce the overall volume of the medical device. In the illustrated implementation, the space is occupied by a communication antenna 395 (FIG. 48) that may be used for telemetric communication to and from the medical device 20c. The communication antenna 395, which includes a core 397 and a coil 398, may be connected to the circuit board 358 within the electronics section 306 by way of pins 364d and 364e on the multi-pin feed-through 354c.

Figure 49:
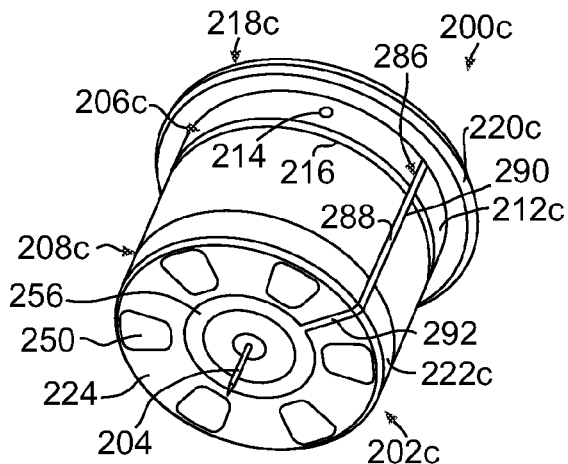
FIG. 49 is a perspective view of a cartridge in accordance with one embodiment of a present invention.
Figure 50:
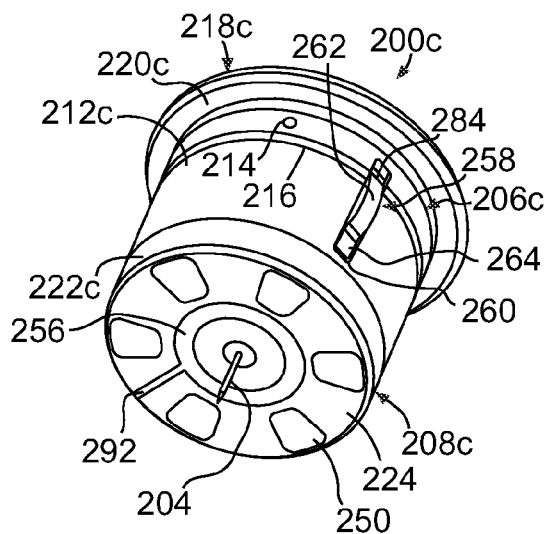
FIG. 50 is another perspective view of the cartridge illustrated in FIG. 49.
Figure 51:
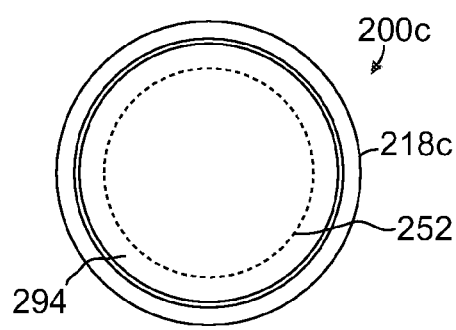
FIG. 51 is a plan view of the cartridge illustrated in FIG. 49.

One example of a replaceable cartridge that includes a power source is generally represented by reference numeral 200c in FIGS. 49-51. Cartridge 200c is substantially similar to cartridge 200 and similar elements are represented by similar reference numerals. The exemplary replaceable cartridge 200c includes a housing 202c, which stores the infusible substance, a needle 204, and a battery 252. Although the present cartridges are not limited to any particular housing structure, the exemplary housing 202c has first and second housing members 206c and 208c and an internal bladder or other functionally related structure (not shown) of, for example, the types described above with reference to FIGS. 13-15. The first housing member 206c has a cylindrical wall 212c, with one or more air holes 214 and a sealing ring 216, and an end wall 218c that is sized such that it extends radially beyond the percutaneous port rounded rim 104 (FIG. 45). The end wall 218c may have a flat flange 220c that rests on the rim 104 (FIG. 44), or a flange that rests on and curls around the rim (as discussed above with reference to FIGS. 13-15). The end wall 218c also includes an indentation 254 (FIG. 52) for the battery 252. The second housing member 208c includes a cylindrical wall 222c and an end wall 224.

The exemplary cartridge 200c may also include one or more sensible members 250 that are sensed by the sensors 124 and 126 to identify rotation of the cartridge 200c relative to the percutaneous port 100c in the manner described in Section VI above. The sensible members 250 may be located on the exterior of the second housing member end wall 224 (as shown), on the exterior of the cylindrical walls 212c and 222c, on the exterior of the end wall 218c, completely or partially embedded within one or more of any of the end and cylindrical walls, or even within the internal volume of the cartridge, depending upon the type of sensible member employed, the location of the associated sensor(s) and the manner in which the sensible member(s) and sensor(s) interact. The sensible members 250 may also be omitted in some implementations.

The exemplary replaceable cartridge 200c is also provided with a contact arrangement that electrically connects the battery 252 to the associated percutaneous port 100c. Referring first to FIGS. 49 and 50, the exemplary replaceable cartridge 200c includes a positive power contact 256 and a negative power contact 258. The positive power contact 256 is coaxial with the needle 204, has an annular shape, and is sized and located such that it will engage the positive power contact 186 on the percutaneous port 100c when the cartridge 200c is inserted into the port, regardless of the rotational orientation of the cartridge relative to the port, while the negative power contact 258 will engage the inner surface of the port tubular wall 102, which is the negative contact for the port 100c. The positive power contact 256, which is also sized and located such that it will not engage the sensor contacts 170a/170b and 172a/172b, may be formed from the electrically conductive materials and manufacturing processes described in Section IV above in the context to the sensible members 250. The negative power contact 258, which may be positioned within an indentation 260 on the housing 202c, includes a bowed portion 262 and a flat portion 264 that is slideable within the indentation. The bowed and flat portions 262 and 264 function like a spring to insure good electrical contact with the percutaneous port tubular wall 102. Suitable examples of electrically conductive materials for the negative power contact 258 include, but are not limited to, copper, nickel, stainless steel and aluminum.

Figure 52:
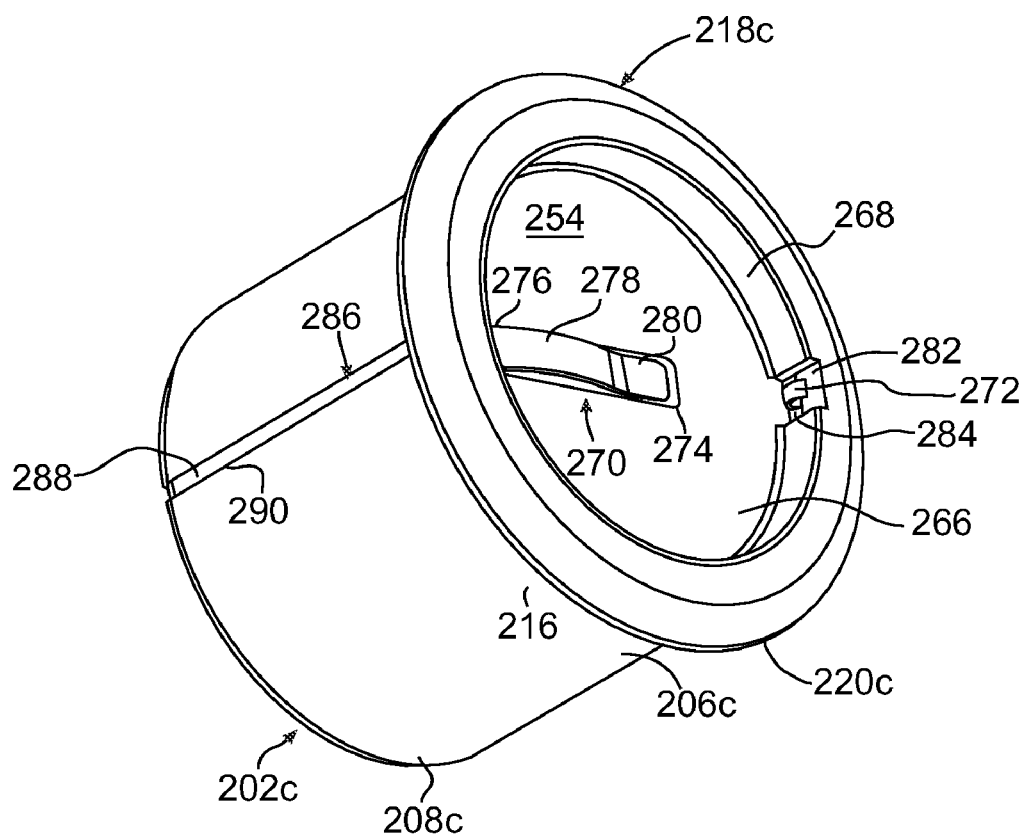
FIG. 52 is a perspective view of the cartridge illustrated in FIG. 49 with the battery and battery cover removed.

Turning to FIG. 52, the battery indentation 254 in the exemplary replaceable cartridge 200c is defined by a bottom wall 266 and side wall 268. Positive and negative battery contacts 270 and 272 are associated with the indentation 254. In the illustrated implementation, the positive battery contact 270 is positioned within an indentation 274 in the bottom wall 266, and includes an anchor portion 276 that is secured to the housing 202c, a bowed portion 278 and a flat portion 280 that is slideable within the indentation. Here too, the bowed and flat portions 278 and 280 function like a spring to insure good electrical contact. The negative battery contact 272 is located within a slot 282 in the side wall 268 and may be secured to the bottom wall 266. The negative battery contact 272 is also integral with the negative power contact 258 in the illustrated embodiment and, to that end, a portion of the negative battery 272 extends through an aperture 284 (FIGS. 50 and 52).

As illustrated in FIGS. 49 and 52, the positive power contact 256 is connected to the positive battery contact 270 in the exemplary implementation by a conductor 286. The conductor 286 includes a first portion 288 located within a groove 290 on the cylindrical walls 212c/222c and a second portion 292 on the end wall 224. The conductor 286 may be formed in any suitable manner before or after the housing 202c is assembled, and will be covered with an electrically insulating material (not shown). An aperture (not shown) may be provided in the end wall 218c or the cylindrical wall 212c in order to allow the positive battery contact 270 and the conductor 286 to be connected to one another.

Figure 53:
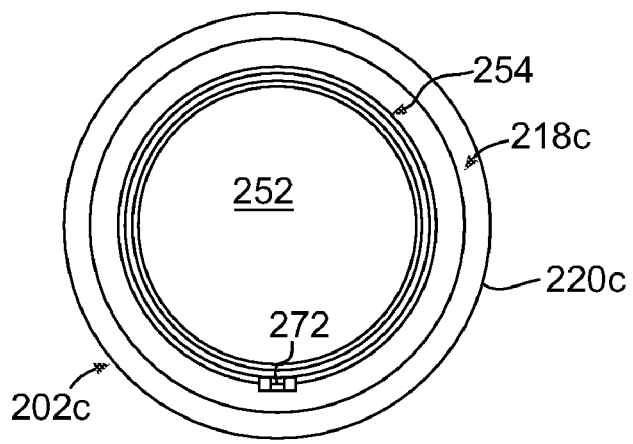
FIG. 53 is a plan view of the cartridge illustrated in FIG. 49 with the battery cover removed.

The battery 252 may be covered after it is inserted into the battery indentation 254 in the manner illustrated in FIG. 53 by any suitable electrically non-conductive water-tight cover. Referring to FIG. 51, the exemplary cover 294 is an adhesive-backed polymer film.

It should be noted here that the medical devices 20a and 20b illustrated in FIGS. 39-43 may be re-configured include cartridges that carry a power supply. It also be noted that other implementations may be configured to be powered by batteries carried with a battery case (e.g. case 116) or batteries carried by a cartridge (e.g. cartridge 300c) in order to accommodate cartridges with and without a power source.

Replaceable cartridges (not shown) may also be configured such that one or more batteries, or other power sources, are carried by the cartridge end wall 224 instead of the end wall 216 (note FIGS. 49-53). Here, the end wall may include one or more battery indentations that protrude into the storage volume 236. The bladder 210 will collapse over and around the indentation(s) as the cartridge is emptied of fluid. A film that carries the sensible members 250, as well as the positive power contact 256 and conductors to connect the batteries to the positive power contact, may be positioned over the end wall and batteries. A negative power contact 258, as well as the associated conductors, may also be provided. In those instances where zinc-air batteries are employed, the film may include air holes that are closed by a removable tape cover. The tape cover is removed when the cartridge is to be inserted into a percutaneous port.

IX. Exemplary Treatment Methodologies

Figure 36A:
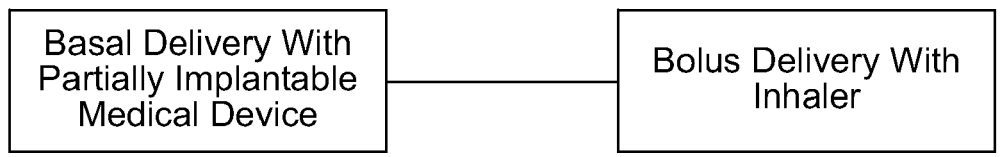
FIG. 36A is a flow chart in accordance with one embodiment of a present invention.

The present inventions also include various methods involving basal delivery of a medication with the present partially implantable medical devices and bolus delivery of medication with the present partially implantable medical devices or with another device, such as an inhaler or an insulin pen. By way of example, but not limitation, one such method may be used to treat diabetes and involves basal delivery of insulin with the present partially implantable medical devices and bolus delivery of insulin, such as mealtime bolus delivery, with present partially implantable medical devices or with an inhaler (note FIG. 36a).

Turning first to the basal delivery of insulin, the partially implantable medical devices described above may be used to transfer liquid insulin, e.g. insulin in liquid form or a suspension of insulin powder in a fluid, from a removable cartridge (e.g. cartridge 200) to the patient. For example, a partially implantable medical device (e.g. device 20) may be positioned subcutaneously, but primarily outside the peritoneal wall, with a delivery tube (e.g. tube 400) extending through the peritoneal wall to the peritoneum, as is illustrated in FIG. 5. So positioned, the insulin will be delivered directly into the peritoneum and the patient will be able to remove the fluid cartridge as necessary by way of the percutaneous port (e.g. port 100).

The patient may be prescribed, and/or otherwise supplied with, a plurality of insulin cartridges of, for example, the type described above (e.g. cartridge 200). The cartridges may be removed from the associated partially implantable medical device and replaced as necessary. In some exemplary treatment regimens, the patient will be instructed to remove a cartridge from the port, and replace the cartridge with a new cartridge, at predetermined time intervals. In other exemplary treatment regimens, the patient could remove the cartridge from the port, refill the cartridge, and place the cartridge back in the port at predetermined time intervals, although this regimen is more susceptible to the risk of infection. The time intervals, which are based on the volume of the particular cartridge being employed and the rate at which the insulin is being dispensed, may be predefined based on the maximum expected rate of consumption. For example, if the fluid storage volume of a cartridge is 1.8 cc, the insulin concentration is 400 units/cc (i.e. 720 units/cartridge), and the maximum basal dosage is 100 units/day, the patient should be instructed to replace the cartridge no less than once a week.

With respect to bolus delivery of inhalable insulin, one exemplary delivery regimen involves the use of powder as a delivery mechanism. In particular, insulin monomers, which can readily be used by the body, may be carried on aerodynamic pH-sensitive particles supplied in powder form. One exemplary particle is the pH-driven self-assembling, self-disassembling particle known as a TECHNOSPHERE® particle and additional information concerning such particles is disclosed in, for example, U.S. Pat. Nos. 6,071,497 and 6,428,771. The powder is administered by way of an inhaler and, in some instances, may be supplied to the patient in a replaceable cartridge (or "dose capsule") that can be loaded into the inhaler. A variety of inhalers may be employed and one exemplary removable cartridge-based inhaler is disclosed in U.S. Pat. Pub. No. 2008/0127970 A1, which is incorporated herein by reference. Accordingly, the patient may be prescribed, and/or otherwise supplied with, an inhaler and prescribed, and/or otherwise supplied with, a plurality of the inhalable insulin cartridges. For example, a patient may be supplied with a one-month supply of inhalable insulin cartridges or a quarterly (i.e. 13-week) supply of inhalable insulin cartridges.

The administration of the mealtime bolus involves the patient drawing air through the inhaler mouthpiece at or just after (e.g. within about 10 minutes) of the beginning of a meal. Air is pulled through the cartridge, which pulls the particles into the air current and out of the inhaler by way of the mouthpiece. When the particles contact the moist lung surface with its neutral pH, the pH-sensitive particles immediately dissolve and release the insulin molecules, which then diffuse across a thin layer of cells into the bloodstream. This process reaches peak levels within 12 to 14 minutes and mimics rapid rise of the first phase insulin profile normally seen in non-diabetic individuals immediately following the beginning of a meal, resulting in marked reductions in postprandial blood glucose without the undesirable persistence of several hours post-meal digestion associated with other insulins.

Other exemplary conditions that may be treated with a partially implantable medical device and an inhaler include, but are not limited to, pain, spasticity and tinnitus. It should also be noted here that the methods described above are not limited to implementations which involve cartridge-based inhalers. Single dosage disposable inhalers and other types of inhalers may also be employed.

Although the present inventions have been described in terms of the preferred embodiments above, numerous modifications and/or additions to the above-described preferred embodiments would be readily apparent to one skilled in the art. It is intended that the scope of the present inventions extend to all such modifications and/or additions and that the scope of the present inventions is limited solely by the claims set forth below.

We claim:

1. A fluid cartridge, comprising:
   a housing including a substantially cylindrical side wall and an end wall and defining a longitudinal axis and an internal volume;
   a needle that extends from the end wall and is not movable relative to the end wall; and
   a plurality of substantially flat electrically conductive sensible members that are not electrically connected to power that flows through other electrically conductive structure on the housing, that are mounted directly on the housing end wall such that each of the sensible members is offset from the other sensible members in a circumferential direction that extends around the longitudinal axis and that are separated from one another by electrically non-conductive regions.

2. A fluid cartridge as claimed in claim 1, further comprising:
   a bladder located within the housing and having an outer surface and an inner surface, the inner surface defining a fluid storage volume having a full state that is substantially equal to the internal volume of the housing.

3. A fluid cartridge as claimed in claim 2, wherein the bladder includes a substantially cylindrical side wall and an end wall, and the substantially cylindrical side wall of the bladder is secured directly to the substantially cylindrical side wall of the housing.

4. A fluid cartridge as claimed in claim 3, wherein
   the housing substantially cylindrical side wall includes an aperture and an external ring that is located between the aperture and the end wall from which the needle extends; and
   the bladder is configured such that the outer surface of the bladder substantially cylindrical side wall abuts the aperture when the fluid storage volume is in the full state.

5. A fluid cartridge as claimed in claim 1, wherein the needle comprises a non-coring needle.

6. A fluid cartridge as claimed in claim 1, wherein the needle defines a longitudinal axis that is substantially coaxial with the housing longitudinal axis.

7. A fluid cartridge as claimed in claim 1, wherein the plurality of sensible members are carried on the exterior of the housing.

8. A fluid cartridge as claimed in claim 1, further comprising:
   a drug within the housing.

9. A fluid cartridge as claimed in claim 1, wherein the sensible members comprise first, second and third sensible members.

10. A fluid cartridge as claimed in claim 9, wherein spacing between the first and second sensible members is equal to spacing between the second and third sensible members.

11. A fluid cartridge as claimed in claim 1, wherein the sensible members are not needles.

12. An apparatus for use with an epidermis, comprising:
    a fluid cartridge including a housing with a substantially cylindrical side wall and an end wall, a needle extending from the housing end wall, and at least one sensible member mounted directly on the housing end wall; and
    a partially implantable medical device including
      a percutaneous port configured to receive the fluid cartridge such that at least a portion of the fluid cartridge housing extends through the epidermis and to permit the fluid cartridge to be rotated from outside the percutaneous port and to be removed from the epidermis independently of the percutaneous port,
      an implantable operative portion including a fluid transfer device, and
      a sensor for sensing the at least one sensible member.

13. An apparatus as claimed in claim 12, wherein the at least one sensible member comprises a plurality of circumferentially spaced sensible members.

14. An apparatus as claimed in claim 13, wherein the sensor comprises first and second circumferentially spaced sensors.

15. An apparatus as claimed in claim 14, wherein the sensible members are sized and spaced such that a single sensible member may be circumferentially aligned with one of the first and second sensors, both of the first and second sensors, or none of the first and second sensors, depending upon the rotational orientation of the fluid cartridge relative to the percutaneous port.

16. An apparatus as claimed in claim 13, wherein the plurality of circumferentially spaced sensible members are separated by non-conductive regions.

17. An apparatus as claimed in claim 16, wherein the sensor comprises first and second circumferentially spaced sensors, each including a pair of electrical contacts.

18. An apparatus as claimed in claim 17, wherein
    the sensible members are electrically conductive, and
    the first and second circumferentially spaced sensors are respectively sized and spaced such that, depending upon the rotational orientation of the fluid cartridge relative to the percutaneous port, a single sensible member can contact both of the electrical contacts in one of the first and second sensors, can simultaneously contact both of the electrical contacts in both of the first and second sensors, and cannot simultaneously contact both of the electrical contacts in both of the first and second sensors.

19. An apparatus as claimed in claim 12, wherein the percutaneous port includes an exterior having a porous region configured to promote soft tissue ingrowth.

20. An apparatus as claimed in claim 12, further comprising:
    a controller operably connected to the sensor and configured to perform a predefined operation in response to sensed rotational movement of the fluid cartridge relative to the percutaneous port.

21. An apparatus as claimed in claim 20, wherein
    the fluid transfer device is configured to transfer fluid at a plurality of flow rates; and the predefined operation comprises increasing or decreasing the flow rate.

22. An apparatus as claimed in claim 12, wherein
the fluid cartridge housing defines an internal volume, and the substantially cylindrical side wall and the end wall abut portions of the percutaneous port; and
the fluid cartridge includes a bladder located within the fluid cartridge housing that has an outer surface and an inner surface, the inner surface defining a fluid storage volume having a full state that is substantially equal to the internal volume of the housing.

23. An apparatus as claimed in claim 12, wherein
the fluid cartridge housing includes a fluid reservoir; and
the at least one sensible member is located on the fluid cartridge housing in spaced relation to the needle.

24. An apparatus as claimed in claim 12, wherein the fluid transfer device includes a pump that receives fluid from the fluid cartridge by way of the percutaneous port and the pump is positioned relative to the percutaneous port such that the pump will be located subcutaneously when the percutaneous port is located percutaneously.

25. An apparatus as claimed in claim 12, wherein
the fluid cartridge housing defines an outer diameter and includes a fluid reservoir; and
the percutaneous port defines an inner diameter that is substantially equal to the outer diameter of the fluid cartridge housing.

26. An apparatus, comprising:
a fluid cartridge including a housing with a substantially cylindrical side wall and an end wall, a needle extending from the housing end wall, and at least one sensible member mounted directly on the housing end wall; and
a partially implantable medical device including
means for percutaneously receiving the fluid cartridge housing such that the fluid cartridge can rotate about an axis defined by the needle,
an implantable operative portion including a pump, and
a sensor for sensing the at least one sensible member.

27. An apparatus as claimed in claim 26, wherein the at least one sensible member comprises a plurality of circumferentially spaced sensible members.

28. An apparatus as claimed in claim 27, wherein the sensor comprises first and second circumferentially spaced sensors.

29. An apparatus as claimed in claim 26, wherein the means for percutaneously receiving the fluid cartridge housing includes an exterior having a porous region configured to promote soft tissue ingrowth.

30. An apparatus as claimed in claim 26, wherein the pump is positioned relative to the means for percutaneously receiving the fluid cartridge housing such that the pump will be located subcutaneously when the means for percutaneously receiving the fluid cartridge housing is located percutaneously.

31. An apparatus as claimed in claim 26, wherein
the fluid cartridge housing defines an internal volume, and the substantially cylindrical side wall and the end wall abut portions of the means for percutaneously receiving the fluid cartridge housing; and
the fluid cartridge includes a bladder located within the fluid cartridge housing that has an outer surface and an inner surface, the inner surface defining a fluid storage volume having a full state that is substantially equal to the internal volume of the housing.

\* \* \* \* \*